United States Patent [19]
Feng et al.

[11] Patent Number: 6,107,549
[45] Date of Patent: Aug. 22, 2000

[54] GENETICALLY ENGINEERED PLANT RESISTANCE TO THIAZOPYR AND OTHER PYRIDINE HERBICIDES

[75] Inventors: Paul C. C. Feng; Thomas G. Ruff, both of Wildwood, Mo.

[73] Assignee: Monsanto Company, St. Louis, Mo.

[21] Appl. No.: 09/264,737

[22] Filed: Mar. 9, 1999

Related U.S. Application Data

[60] Provisional application No. 60/077,377, Mar. 10, 1998.
[51] Int. Cl.⁷ ............................ C12N 15/29; C12N 15/82; A01H 3/00; A01H 4/00
[52] U.S. Cl. .......................... 800/300; 800/295; 800/298; 800/278; 536/241; 536/236; 536/23.5; 435/468; 435/419; 435/320
[58] Field of Search .................................... 800/295, 298, 800/278, 300; 536/23.6, 24.1, 23.5; 435/468, 419, 320.1

[56] References Cited

U.S. PATENT DOCUMENTS 5,463,175  10/1995  Barry et al. ............................. 800/205

OTHER PUBLICATIONS

Feng, Paul C.C. et al., "Engineering Plant Resistance to Thiazopyr herbicide via expression of a novel esterase deactivation enzyme," Pesticide Biochemistry and Physiology, p. 89–103, (Mar. 8, 1998).

Korza, G. et al., "Complete covalent structure of 60–kDa esterase isolated from 2,3,7,8–tetrachlorodibenzo–p–dioxin– induced rabbit liver microsomes," The Journal of Biological Chemistry, vol. 263 (No. 7), p. 3486–3495, (Mar. 8, 1988).

Ozols,J., "Isolation and characterization of a 60–kilodalton glycoprotein esterase from liver microsomal membranes.," The Journal of Biological Chemistry, vol. 262 (No. 31) p. 15,316–15,321, (Nov. 5, 1987).

Feng et al. Xenobiotica. vol. 25, No. 1, pp. 27–35, 1995.

*Primary Examiner*—Lynette R. F. Smith
*Assistant Examiner*—Thomas Haas
*Attorney, Agent, or Firm*—Pharmacia Corporation; Timothy K. Ball; Dennis R. Hoerner, Jr.

[57] ABSTRACT

Esterase-encoding recombinant plant genes are utilized to achieve metabolic deactivation as a means to genetically engineer plant resistance to pyridine herbicides. The esterase/pyridine system provided is further useful as a selection system for the identification of transformed plant cells.

32 Claims, 9 Drawing Sheets

```
RLE1   1 HPSAPPVVDTVKGKVLGKFVSLEGFAQPVAVFLGVPFAKPPLGSLRFAPP  50
         ||||||||||||||||||||||||||||||||||||||||||||||||||
RLE3   1 HPSAPPVVDTVKGKVLGKFVSLEGFAQPVAVFLGVPFAKPPLGSLRFAPP  50

51 QPAESWSHVKNTTSYPPMCSSDAVSGHMLSELFTNRKENIPLKFSEDCLY 100
         |||||||||||||||||||| |||||||||||||||||||||||||||||
      51 QPAESWSHVKNTTSYPPMCSQDAVSGHMLSELFTNRKENIPLKFSEDCLY 100

101 LNIYTPADLTKRGRLPVMVWIHGGGLMVGGASTYDGLALSAHENVVVVTI 150
         ||||||||||||||||||||||||||||||||||||||||||||||||||
     101 LNIYTPADLTKRGRLPVMVWIHGGGLMVGGASTYDGLALSAHENVVVVTI 150

151 QYRLGIGGFGFNIDE........LFLVAVNRWVQDNIANFGGDPGSVTIF 192
         ||||||  ||  ||          |    |||||||||||||||||||||
     151 QYRLGIWGFFSTGDEHSRGNWGHLDQVRALRWVQDNIANFGGDPGSVTIF 200

193 GESAGGQSVSILLLSPLTKNLFHRAISESGVALLSSLFRKNTKSLAEKIA 242
         ||||||||||||||||||||||||||||||||||||||||||||||||||
     201 GESAGGQSVSILLLSPLTKNLFHRAISESGVALLSSLFRKNTKSLAEKIA 250

243 IEAGCKTTTSAVMVHCLRQKTEEELMEVTLKMKFMALDLVGDPKENTAFL 292
         ||||||||||||||||||||||||||||||||||||||||||||||||||
     251 IEAGCKTTTSAVMVHCLRQKTEEELMEVTLKMKFMALDLVGDPKENTAFL 300

293 TTVIDGVLLPKAPAEIYEEKKYNMLPYMVGINQQEFGWIIPMQMLGYPLS 342
         ||||||||||||||||||||||||||||||||||||||||||||||||||
     301 TTVIDGVLLPKAPAEILAEKKYNMLPYMVGINQQEFGWIIPMQMLGYPLS 350

343 EGKLDQKTATELLWKSYPIVNVSKELTPVATEKYLGGTDDPVKKKDLFLD 392
         ||||||||||||||||||||||||||||||||||||||||||||||||||
     351 EGKLDQKTATELLWKSYPIVNVSKELTPVATEKYLGGTDDPVKKKDLFLD 400

393 MLADLLFGVPSVNVARHHRDAGAPTYMYEYRYRPSFSSDMRPKTVIGDHG 442
         ||||||||||||||||||||||||||||||||||||||||||||||||||
     401 MLADLLFGVPSVNVARHHRDAGAPTYMYEYRYRPSFSSDMRPKTVIGDHG 450

443 DEIFSVLGAPFLKEGATEEEIKLSKMVMKYWANFARNGNPNGEGLPQWPA 492
         ||||||||||||||||||||||||||||||||||||||||||||||||||
     451 DEIFSVLGAPFLKEGATEEEIKLSKMVMKYWANFARNGNPNGEGLPQWPA 500

493 YDYKEGYLQIGATTQAAQKLKDKEVAFWTELWAKEAARPRETEHIEL 539
         |||||||||||||||||||||||||||||||||||||||||||||||
     501 YDYKEGYLQIGATTQAAQKLKDKEVAFWTELWAKEAARPRETEHIEL 547
```

FIGURE 2

```
   1  ATGGCAAGAC TCTACCCACT CGTGTGGCTC TTCCTTGCAG CCTGCACCGC
  51  ATGGGGTCAC CCCTCCGCAC CACCTGTGGT TGACACTGTA AAGGGGAAAG
 101  TCCTGGGGAA GTTCGTCAGC TTAGAAGGAT TTGCACAGCC CGTGGCCGTC
 151  TTCCTGGGAG TCCCCTTCGC CAAGCCCCCT CTTGGATCCC TGAGGTTTGC
 201  ACCACCACAG CCTGCAGAAT CATGGAGCCA CGTGAAGAAC ACCACCTCCT
 251  ACCCTCCCAT GTGCTCCCAG GACGCAGTAT CAGGGCATAT GCTCTCGGAG
 301  CTCTTCACCA ACAGAAAAGA GAACATCCCT CTTAAGTTTT CTGAAGACTG
 351  CCTTTACCTG AATATTTACA CCCTGCTGA CCTGACAAAG AGAGGCAGGC
 401  TGCCGGTGAT GGTGTGGATC CATGGAGGTG GTCTGATGGT GGGTGGAGCA
 451  TCAACCTATG ATGGCCTGGC TCTTTCTGCC CATGAGAACG TGGTGGTGGT
 501  GACCATTCAG TACCGCCTGG GCATCTGGGG ATTCTTCAGC ACAGGAGATG
 551  AGCACAGCCG AGGGAACTGG GGTCACTTGG ACCAGGTGCG TGCGCTGCGG
 601  TGGGTCCAGG ACAATATTGC CAACTTTGGA GGGGACCCAG GCTCTGTGAC
 651  CATCTTTGGA GAGTCAGCAG GAGGTCAAAG TGTCTCTATC CTTCTATTAT
 701  CCCCCCTGAC CAAGAATCTC TTCCATCGAG CAATTTCCGA GAGTGGCGTG
 751  GCCCTCCTTT CCAGTCTCTT CAGGAAGAAC ACCAAGTCCT TGGCTGAGAA
 801  AATTGCCATC GAAGCTGGGT GTAAAACCAC CACCTCGGCT GTCATGGTTC
 851  ACTGCCTGCG CCAGAAGACA GAGGAAGAAC TCATGGAGGT GACATTGAAA
 901  ATGAAATTTA TGGCTCTAGA TCTAGTTGGC GACCCCAAAG AGAACACCGC
 951  CTTCCTGACC ACTGTGATTG ATGGGGTGCT GCTGCCAAAA GCACCTGCAG
1001  AGATTCTGGC AGAGAAGAAA TACAACATGC TGCCCTACAT GGTGGGAATC
1051  AACCAGCAAG AGTTTGGCTG GATTATCCCA ATGCAAATGC TGGGCTATCC
1101  ACTCTCTGAA GGCAAACTGG ACCAGAAGAC AGCTACAGAA CTCTTGTGGA
1151  AGTCCTACCC CATTGTCAAT GTCTCTAAGG AGCTGACTCC AGTGGCCACT
1201  GAGAAGTATT TAGGAGGGAC AGATGACCCT GTCAAAAGA AAGACTTGTT
1251  CCTGGACATG CTTGCAGATT TGTTATTTGG TGTCCCATCT GTGAATGTGG
1301  CTCGTCACCA CAGAGATGCT GGAGCCCCCA CCTATATGTA TGAGTATCGG
```

FIGURE 7A

```
1351  TATCGCCCAA GCTTCTCATC AGACATGAGA CCCAAGACAG TGATAGGGGA

1401  CCATGGAGAT GAGATCTTCT CTGTCTTAGG AGCCCCGTTT TTAAAAGAGG

1451  GTGCCACAGA AGAGGAGATC AAACTGAGCA AGATGGTGAT GAAATACTGG

1501  GCCAACTTTG CTAGGAATGG GAATCCCAAT GGAGAAGGGC TTCCTCAATG

1551  GCCAGCATAT GACTACAAGG AAGGTTACCT GCAGATTGGA GCCACCACCC

1601  AGGCAGCCCA GAAACTGAAA GACAAGGAAG TGGCTTTCTG GACTGAGCTC

1651  TGGGCCAAGG AGGCAGCAAG GCCACGTGAG ACTGAACACA TCGAGCTGTA

GENETICALLY ENGINEERED PLANT RESISTANCE TO THIAZOPYR AND OTHER PYRIDINE HERBICIDES

RELATED APPLICATION INFORMATION

This application claims the benefit of priority and is filed within one year of the application date of U.S. Provisional Patent Application Ser. No. 60/077,377, filed Mar. 10, 1998.

BACKGROUND OF THE INVENTION

Genetic engineering now provides the tools to begin to develop herbicide resistance crops, thereby offering valuable options in effective crop management. The ability to introduce herbicide resistance into plants extends the use of desirable, non-selective herbicides to sensitive crop species, and offers numerous economic and environmental advantages (Schulz et al., 1990). An excellent example of this is the commercial introduction of glyphosate resistance in a variety of crops.

The pyridine family of herbicides can control narrow-leaf and small seeded broad-leaf weeds under pre-emergence application (See for example, U.S. Pat. Nos. 4,826,532; 4,747,871; 4,692,184; 4,885,026; and 5,019,153). Cell biology studies using the pyridine dithiopyr suggest that disruption of cell division is the mode of action of the pyridine herbicides (Armbruster et al., 1991), most likely by disrupting microtubule organization (Armbruster et al., 1988). Seeds germinated in the presence of pyridine herbicides show characteristic inhibition of root elongation and swelling of meristematic zones. Thiazopyr is predominantly metabolized in both animals (Feng et al., 1994a) and plants (Feng et al., 1995a) via oxidations at the sulfur or carbon atoms in the thiazoline ring. The resulting initial metabolites have a transient existence and are further degraded to polar and/or acidic metabolites (McClanahan et al., 1995). A key reaction is de-esterification of the methylester functional group to form the monoacid metabolite which is virtually devoid of any herbicidal activity (Feng et al., 1995b). It has been demonstrated in animals that de-esterification can occur either by oxidation (Feng et al, 1994b) or hydrolysis (Feng et al., 1995b), both reactions being catalyzed by liver enzymes (Feng et al. (1994b)). Feng et al. (1995b) were particularly interested in esterases due to their lack of requirement for cofactors during catalysis and their ubiquitous presence in nature hydrolyzing both endogenous substrates and xenobiotics (Leinweber, 1987). Thiazopyr metabolism in plants differs from animals in that the monoacid appears to be produced exclusively via the oxidation pathway (Feng et al., 1995). Using inhibitors of monooxygenase enzymes, Feng et al. (1995a) demonstrated in planta suppression of thiazopyr metabolism which translated to enhanced bioefficacy.

Thiazopyr shows little plant selectivity which limits its use in many important agronomic crops. The present application describes the purification of a novel thiazopyr esterase, and the subsequent cloning and expression of a gene encoding the esterase in plants. Tobacco and tomato plants transformed to express the pyridine-esterase confirm that esterase-mediated deactivation of pyridines is a viable approach for engineering herbicide resistance in plants.

SUMMARY OF THE INVENTION

This invention broadly concerns the genetic manipulation of plants so as to confer herbicide tolerance and herbicide resistance. The compositions and methods described and exemplified herein provide a metabolic deactivation approach for generating herbicide tolerant or herbicide resistant plants wherein plants are engineered to rapidly deactivate herbicidal pyridines thereby minimizing or eliminating herbicidal phytotoxicity. The availability of herbicide resistant or herbicide tolerant crops as described herein provides a very selective and powerful means for effective weed control.

In addition, the invention described herein is further applicable for use as a cell selection system whereby plant cells, or conceivably other types of cells too, which have been transformed to contain a desired polynucleotide molecule encoding a pyridine esterase can be selectively isolated from non-transformed cells which do not contain the polynucleotide molecule.

Therefore, in accordance with one aspect of the present invention a recombinant polynucleotide molecule comprising a plant functional promoter operably linked to a polynucleotide sequence encoding an esterase that catalyzes the hydrolysis of an alkyl ester group of a pyridine compound, wherein said pyridine compound is an agent used to control or modify plant growth. The polynucleotide molecule comprising the esterase coding sequence can be isolated at least from the liver of mammalian species such as rabbit, porcine, bovine, pigeon, goat, horse, or sheep. In addition, esterases isolated from other species, in particular those esterases preferably isolated from plant or bacterial species and which inactivate pyridine herbicides are also considered to be within the scope of the present invention. The polynucleotide molecule comprising the esterase coding sequence as specifically defined herein comprises an esterase isolated from rabbit liver, designated herein as RLE3. RLE3 preferably inactivates the pyridine herbicides thiazopyr or MON14300.

In accordance with another aspect of the present invention, there is provided a recombinant polynucleotide molecule comprising:
 a promoter that functions in plant cells to cause the production of an RNA molecule; operably linked to,
 a polynucleotide sequence encoding an esterase that catalyzes the hydrolysis of an alkyl ester group of an herbicidally active pyridine; and
 a 3' non-translated region that functions in plant cells to cause the polyadenylation of the 3' end of the RNA molecule.

The esterase coding sequence used in a polynucleotide or DNA molecule of this invention is one that is capable of converting an herbicidally active pyridine to a form having reduced herbicidal or phytotoxic activity. This is accomplished by the hydrolytic de-esterification of one or more alkyl ester groups of a pyridine that contains such groups. Examples of alkyl ester groups which are within the scope of the present invention include methyl ester, ethyl ester, propyl ester, butyl ester, butyryl ester, pentyl ester, dodecyl ester, and valeryl ester. Preferably, the esterase coding sequence is isolated from rabbit, porcine, bovine, pigeon, goat, horse, or sheep.

In accordance with another aspect of the invention, there is provided a method for selection of transformed plant cells, comprising the steps of
 transforming plant cells with a recombinant polynucleotide molecule which comprises:
  a promoter that functions in plant cells to cause the production of an RNA molecule; operably linked to,
  a polynucleotide sequence encoding an esterase that catalyzes the hydrolysis of an alkyl ester group of an herbicidally active pyridine; and a 3' non-translated region that functions in plant cells to cause the polyadenylation of the 3' end of the RNA molecule; and selecting those cells which survive exposure to the pyridine herbicide.

In accordance with another aspect of the invention, there is provided a method for the production of pyridine resistant transgenic plants, comprising the steps of:

transforming plant cells with a polynucleotide molecule comprising:
   a promoter that functions in plant cells to cause the production of an RNA molecule; operably linked to,
   a polynucleotide sequence encoding an esterase that catalyzes the hydrolysis of an alkyl ester group of an herbicidally active pyridine;
   a 3' non-translated region that functions in plant cells to cause the polyadenylation of the 3' end of the RNA molecule.

selecting transformed cells; and regenerating a plant from the transformed plant cells.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2 compares the amino acid sequences of the published amino acid sequence of rabbit liver esterase isozyme 1 (RLE1) with the cDNA of cloned pyridine esterase (RLE3). There was an 95% overall identity with the majority of the divergence localized in one region near the N-terminus. The RLE3 amino acid sequence shown contains a 19 amino acid signal peptide as described herein, so that the esterase amino acid sequence begins with the histidine at position 20, and aligns with the histidine at the amino terminus of the RLE1 amino acid sequence. Sequence surrounded by blocks indicates divergent sequences between the two esterases.

FIG. 7 shows the DNA sequence of the rabbit RLE3 cDNA, wherein the RLE3 coding sequence extends from nucleotide 58 through nucleotide 1701. Nucleotides in position 1 through 57 encode the signal peptide as set forth in FIG. 2, represented by amino acids 1 through 19.

BRIEF DESCRIPTION OF THE SEQID NO.'S

Figure 1:
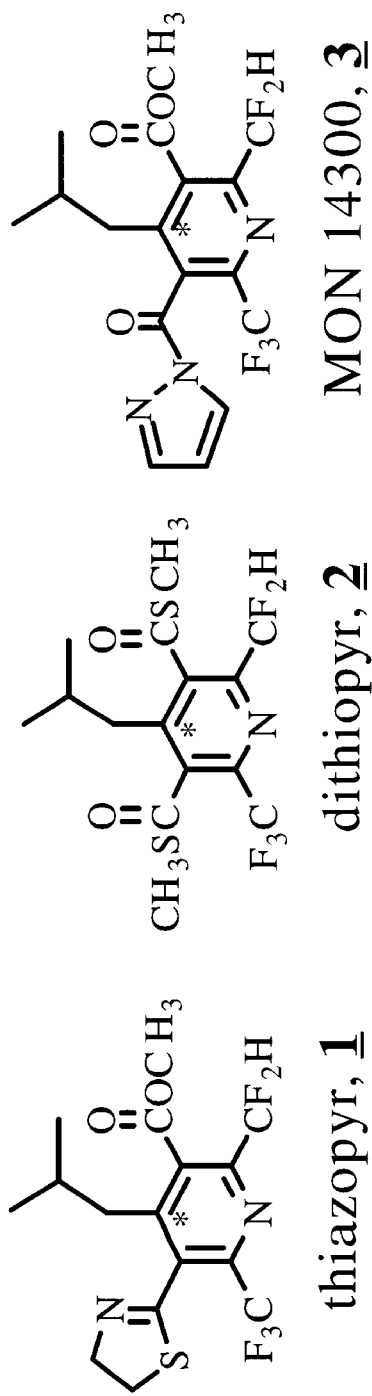
FIG. 1 illustrates the structures of the pyridine herbicides thiazopyr, dithiopyr, and MON 14300.
Figure 3:
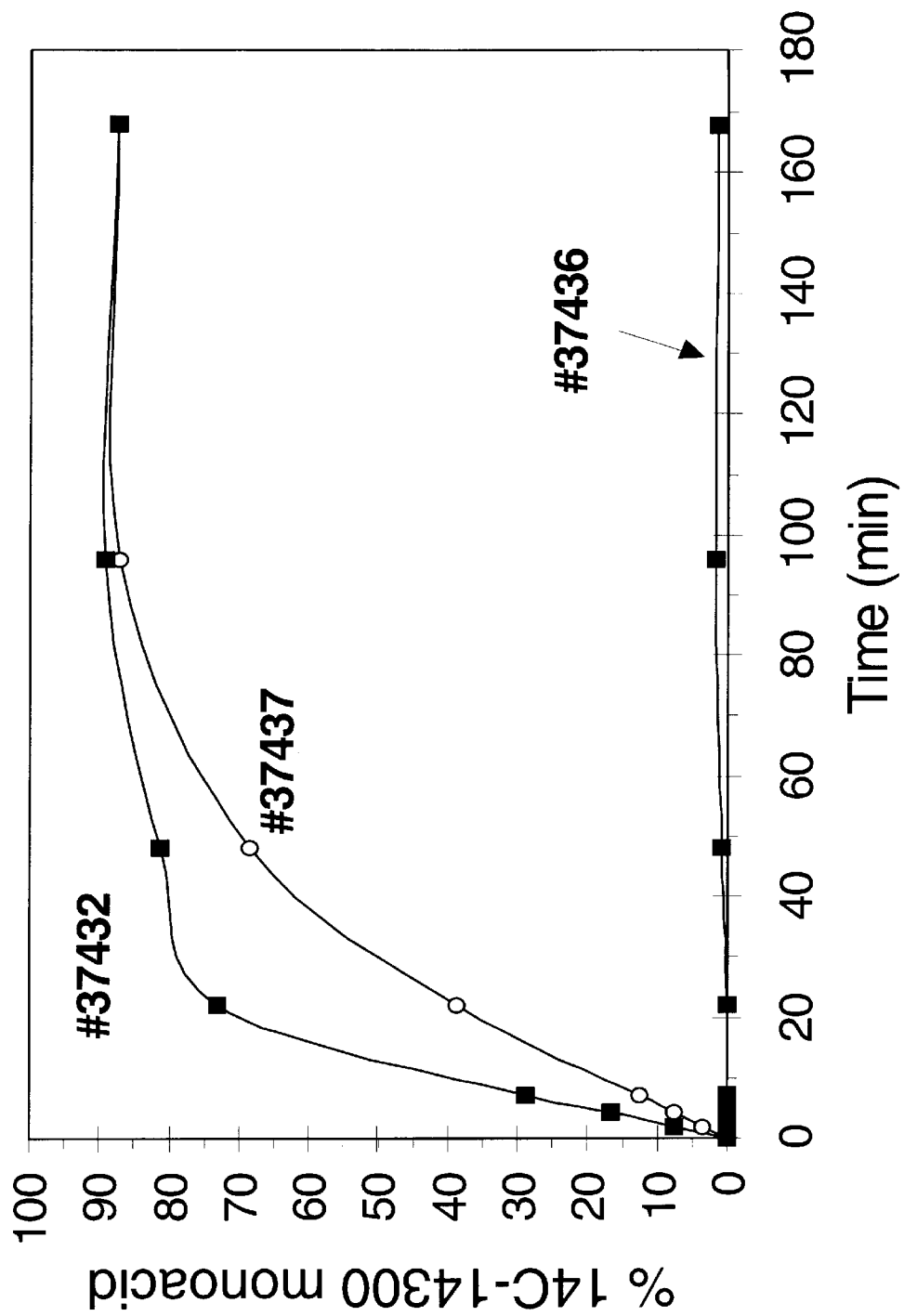
FIG. 3 illustrates the kinetics of pyridine-esterase activity against [$^{14}$C]MON 14300 in extracts prepared from transgenic tobacco seedlings. Lines expressing the pyridine-esterase (#37432 and #37437) showed efficient hydrolysis of MON 14300 to its monoacid metabolite. The non-expressing line (#37436) showed no hydrolysis.

SEQ ID NO:1: amino acid sequence of rabbit liver esterase RLE1 (Korza et al., J. Biol. Chem. 263:3489–3495) 1988.

SEQ ID NO:2: amino acid sequence of rabbit liver esterase RLE3 as disclosed herein.

SEQ ID NO:3: native DNA coding sequence of rabbit liver esterase RLE3 as disclosed herein.

SEQ ID NO:4: amino terminal degenerate synthetic primer based on published amino acid sequence of rabbit liver esterase isozyme 1 RLE1 (Ozols, 1987).

SEQ ID NO:5: carboxy terminal degenerate synthetic primer based on published amino acid sequence of rabbit liver esterase isozyme 1 RLE1 (Ozols, 1987).

SEQ ID NO:6: synthetic sequence coding for ER signal peptide based on Robbi et al., 1990.

SEQ ID NO:7: synthetic inverse strand sequence coding for ER signal peptide based on Robbi et al., 1990.

SEQ ID NO:8: synthetic thermal amplification sequence homologous to RLE3 divergent region flanking sequence SEQ ID NO:9: synthetic thermal amplification sequence homologous to RLE1 divergent region flanking sequence SEQ ID NO:10: synthetic site specific mutagenesis primer for RLE3 amino acid sequence conversion of Gln71Ser SEQ ID NO:11: synthetic site specific mutagenesis primer for RLE3 amino acid sequence conversion of Leu309Tyr and Ala310Glu

DESCRIPTION OF ILLUSTRATIVE EMBODIMENTS

The inventors have successfully engineered pyridine resistance or pyridine tolerance in transgenic plants via metabolic deactivation. Their efforts to engineer plant resistance to pyridines have involved the identification of an inactive metabolite of thiazopyr, identification and isolation of an enzyme capable of catalyzing conversion to this inactive metabolite, and introduction of this activity into plants via genetic engineering. The inventors demonstrate herein that transgenic plants expressing a pyridine-esterase showed esterase activity against pyridine herbicides sufficient to confer resistance. Recombinant tobacco and tomato plant lines expressing pyridine esterase exhibited measurable resistance to thiazopyr in growth chamber and green house tests. In addition, transgenic tomato seeds showed increased rates of germination in the field with PPI (pre-plant incorporation) application of thiazopyr.

Recombinant Polynucleotide Molecules

In accordance with one aspect of the invention, there are provided recombinant, plant expressible polynucleotide molecules, for use in the production of pyridine resistant transgenic plants. A polynucleotide molecule of the present invention, which may also be referred to herein as a recombinant plant gene, contains a coding sequence in the linear conformation of nucleotide bases which can be translated to produce an esterase enzyme which hydrolyzes an alkyl ester group of a herbicidally active pyridine. Upon hydrolysis of the alkyl ester group, the resulting acid form of the pyridine becomes largely devoid of herbicidal activity. Thus, the esterase essentially catalyzes the conversion of an herbicidally active or phytotoxic pyridine to an inactive non-herbicidal or non-phytotoxic form.

In general, a recombinant plant gene comprises, operably linked from the 5' to the 3' end: (1) a promoter region that causes the production of an RNA molecule; (2) a polynucleotide sequence which encodes a desired RNA and/or protein; and (3) a 3' non-translated region. A 5' non-translated sequence may also be present and localized between the promoter and the coding sequence. An alternative recombinant plant gene which is within the scope of the present invention comprises a plant chloroplast or plastid functional promoter operably linked to a polynucleotide sequence encoding a pyridine esterase. Such recombinant genes are known in the art, for example, plastid or chloroplast functional recombinant genes as provided for in Maliga et al. (U.S. Pat. No. 5,451,513; 1995) which is herein incorporated by reference.

The region of a gene referred to as the "promoter" is responsible for regulating transcription of a polynucleotide sequence, typically a DNA sequence, into RNA. Promoters comprise a portion of the DNA sequence found upstream of (5' to) a desired coding sequence, and by providing one or more recognition sites for binding of RNA polymerase and/or other factors necessary for transcription initiation, regulate expression of desired DNA sequences which are linked 3' to the promoter, resulting in RNA synthesis of the linked sequences. RNA which is synthesized can be of several different functional types including but not limited to transfer RNA (tRNA), messenger RNA (mRNA), ribosomal RNA (rRNA), and antisense RNA (asRNA). The promoter used in a recombinant plant gene of the invention is selected so as to provide sufficient spatially or temporally regulated transcriptional activity to achieve desired expression levels of the gene or gene(s) of interest. Plant functional promoters can thus regulate expression in either a temporal and/or a spatial manner, or can be constitutive. By temporal regulation, it is meant that a desired promoter can be selected so that expression from that promoter is observed to occur only at particularized times during plant growth. For example, a light regulated promoter may be functional or substantially functional when the plant is exposed to light, or conversely may be nonfunctional or substantially nonfunctional, ie repressed, when the plant is exposed to light. Alternatively, a promoter may be selected to be functional or substantially functional during a particularized period of time during plant growth and development, such as during leaf tip extension, flower development, during root or shoot extension, during seed development, or during seed germination. By spatial regulation, it is meant that a desired promoter can be selected so that expression from that promoter is observed to occur only within particularized plant tissues, such as only in leaf parts, within flower parts, within root parts, within meristem tissue, within flower tissue, or within seed tissue, or only within particularized cells within a selected plant tissue. Thus, promoters may be selected to be both temporally and spatially regulated, reserving expression of a linked gene to a particular group of cells or tissue during a particular period of time. Constitutive expression from a selected promoter is also contemplated, wherein expression is not particularly regulated, but is not limited by temporal or spatial constraints. However, constitutive expression may be limited to a particular tissue type or group of cells within a plant, so that a gene product produced from such expression is accumulated within said tissues and not elsewhere within the plant. One skilled in the art will readily recognize that there are various combinations of plant expression that can be obtained ranging from constitutive to minimal tissue type specific plant promoter expression. By substantially functional or substantially nonfunctional, it is meant that it is possible to detect a gene product produced as a result of expression from the initiated transcription of said gene. For example, the presence and quantity of an RNA produced from the expression of a particular polynucleotide linked to a promoter can be monitored using radio-isotope probes or radio-isotope or chemically labeled RNA precursors detectable by fluoroscopy or radiography, by RNAse protection methods, or by methods utilizing reverse transcriptase thermal amplification. Alternatively, the presence and quantity of a protein synthesized as a result of transcription of a linked gene from a promoter can be monitored so long as the protein produced has some activity which can be measured, typically by catalyzing a measureable enzyme-substrate reaction. Such methods are well known in the art. Immunological methods are also contemplated for detecting the presence and quantity of a protein so synthesized, and these methods too are well known in the art.

Numerous plant-functional promoters are known in the art and may be obtained from a variety of sources such as plants or plant viruses and may include, but are not limited to, the cauliflower mosaic virus (CaMV) 35S promoter (Odell et al. 1985), the Figwort mosaic virus (FMV) 35S (Sanger et al. 1990), the sugarcane bacilliform virus promoter (Bouhida et al., 1993), the commelina yellow mottle virus promoter (Medberry and Olszewski 1993), the light-inducible promoter from the small subunit of the ribulose-1,5-bis-phosphate carboxylase (ssRUBISCO) (Coruzzi et al., 1984), the rice cytosolic triosephosphate isomerase (TPI) promoter (Xu et al. 1994), the adenine phosphoribosyltransferase (APRT) promoter of Arabidopsis (Moffatt et al. 1994), the rice actin 1 gene promoter (Zhong et al. 1996), and the mannopine synthase and octopine synthase promoters (Ni et al. 1995). All of these promoters have been used to create various types of plant-expressible recombinant DNA constructs. Comparative analysis of constitutive promoters by the expression of reporter genes such as the uida (β-glucuronidase) gene from $E.\ coli$ has been performed with many of these and other promoters (Li et al. 1997; Wen et al. 1993). Bacterial promoters have also been shown to be functional when localized to the plastid or chloroplast stroma and/or lumen (Daniell et al., U.S. Pat. No. 5,693,507; 1997, incorporated by reference).

Depending on the particular application, other useful promoters may include those which are tissue-specific, tissue-enhanced, developmentally regulated, etc. Examples of these types of promoters are also known in the art.

The coding sequence of a recombinant polynucleotide molecule according to this aspect of the invention encodes an esterase enzyme which catalyzes the hydrolytic de-esterification of an alkyl ester-containing pyridine. Hydrolysis of an alkyl ester group from an herbicidally active or plant phytotoxic pyridine can in many instances result in an acid form of the pyridine that possesses greatly reduced herbicidal or phytotoxic activity. Preferred esterase genes for use in the present invention include, but are not limited to, those derived from porcine, rabbit, pigeon, goat, horse and sheep, since these are known to contain the desired hydrolytic activity. It is possible that a preferred esterase will be of microbial origin with high specificity to thiazopyr and ease of expression in plants. However, unmodified bacterial genes are often poorly expressed in transgenic plants, thus, such genes should be modified to provide coding sequences which more uniformly represent plant-like, 'plantized', or plant recognizable codons for more efficient translation into functional enzymes of the present invention.

The 3' non-translated region which is employed in a polynucleotide or DNA molecule described herein generally causes transcription termination and polyadenylation of the 3' end of the transcribed mRNA sequence. The 3' non-translated region may be derived from a source that is native or that is heterologous with respect to the other non-translated and/or translated elements present on the DNA molecule. Numerous 3' regions are known and readily available to the skilled individual. However, such sequences are not necessary, essential, or functional when plastid or chloroplast localized expression is contemplated.

Other elements are frequently used and/or modifications made to manipulate the levels/targets/timing of expression of the recombinant gene in plant cells, as is known by the skilled individual in this art. Therefore, in addition to those elements discussed above, a recombinant DNA molecule of the present invention can also include chloroplast sequestering/targeting sequences and or additional regulatory elements such as introns and enhancer elements, etc. (for review on optimizing transgene expression, see (Koziel et al., 1996). For example, improvements in expression have been obtained by using enhancer sequences inserted either upstream or downstream from the promoter. Still further improvements have been achieved, especially in monocot plants, by gene constructs which have introns in a 5' non-translated leader positioned between the promoter and the structural coding sequence. For example, (Callis et al., 1987) reported that the presence of alcohol dehydrogenase (Adh-1) introns or Bronze-1 introns resulted in higher levels of expression. Mascarenkas et al. (1990) reported a 12-fold enhancement of CAT expression by use of the Adh intron. Other introns suitable for use in the polynucleotide molecules of the invention include, but are not limited to, the sucrose synthase intron (Vasil et al., 1989), the TMV omega intron (Gallie et al., 1989), the maize hsp70 intron, and the rice actin intron (McElroy et al., 1990).

A wide variety of cloning methods and tools are commercially available and have been extensively described; see for example, (Sambrook et al., 1989); (Birren et al., 1996). Such methods are well known and can be readily used by the skilled individual in constructing the DNA molecules.

In constructing a recombinant DNA molecule for use in the methods of the invention, the various components or fragments thereof are typically inserted using methods known to those of skill in the art into a convenient cloning vector which is capable of replication in a bacterial host, such as *E. coli*. Numerous vectors exist that have been described in the literature. After each subcloning, the vector may be isolated and subjected to further manipulation, such as restriction digestion, insertion of new fragments, ligation, deletion, resection, insertion, in vitro mutagenesis, addition of polylinker fragments, and the like, in order to provide a vector which will meet a particular need.

Pyridine Esterases as Selectable Markers

A recombinant polynucleotide or DNA molecule for use in the production of transformed plant cells and/or transgenic plants typically includes a selectable marker. These markers make it possible to selectively isolate transformed plant cells, i.e., those that contain the recombinant DNA molecule of interest, from the non-transformed cells that do not contain the DNA. Examples of such include, for example, a neomycin phosphotransferase (NPTII) gene (Potrykus et al., 1985), which confers kanamycin resistance. Cells expressing the NPTII gene can be selected using an appropriate antibiotic such as kanamycin or G418. Other commonly used selectable markers include the bar gene which confers bialaphos resistance; a mutant EPSP synthase gene (Hinchee et al., 1988) or a glyphosate oxidase (GOX) gene (Barry et al., U.S. Pat. No. 5,463,175; 1995) which both confer glyphosate resistance or glyphosate tolerance; a nitrilase gene which confers resistance to bromoxynil (Stalker et al., 1988); a mutant acetolactate synthase gene (ALS) which confers imidazolinone or sulfonylurea resistance; and a methotrexate resistant DHFR gene (Thillet et al., 1988).

In accordance with another aspect of the invention, the pyridine/esterase system described herein provides a valuable means by which transformed plant cells can be selected/isolated from untransformed plant cells by exposing the cells to an amount of an herbicidally active pyridine sufficient to be toxic to non-transformed cells but essentially non-toxic to transformed cells. A plant functional DNA molecule which encodes a pyridine esterase can be included as a selectable marker gene in essentially any plant transformation vector using techniques well known and readily available to individuals skilled in this art. Using such an approach, plant cells transfected with a plant transformation vector comprising an esterase gene as a selectable marker are easily selected on the basis of their ability to survive in the presence of a pyridine herbicide.

Pyridine Resistant Transgenic Plants

According to another aspect of this invention, there is provided a method of introducing herbicide resistance or herbicide tolerance into plants using a recombinant DNA molecule of the invention by transforming plant cells with the DNA molecule and regenerating plants therefrom.

Transgenic plants expressing the desired esterase will exhibit resistance to pyridine herbicides. The method is applicable to many herbicidally active pyridines provided (1) the pyridine contains an alkyl ester group and (2) the hydrolysis of that alkyl ester group causes a reduction in herbicidal activity.

The term 'herbicide' as used herein is meant to include an agent which may be used to destroy or inhibit plant growth, which is also meant to include an agent which when applied to plant tissues is able to induce control or regulation of plant growth or to modify plant growth. Agents which are capable of plant growth control or modification are typically those which exert a negative preferential growth effect on the particular plant tissue. Pyridine herbicides are characterized by their extremely high lipophilicity. Most of the pyridine herbicides contain a carboxy methylester functional group which when hydrolyzed generates an acidic metabolite that is considerbly more hydrophilic. It is believed that it is this change from a lipohilic to a hydrophilic molecule that results in the loss of herbicidal activity. Indeed, the acidic metabolites of many pyridine herbicides including thiazopyr and MON14300 have been shown to be herbicidally inactive during spray tests.

In addition, there are other classes of herbicides which contain carboxymethylester functional groups that are hydrolyzable by the esterases described herein (Assure, Acclaim, Fusilade, etc.). These herbicides can be deactivated following esterase hydrolysis in a manner similar to the pyridines.

In arriving at the pyridine resistant transgenic plants described and exemplified herein, this work has generated several interesting and unexpected observations. The first is the lack of plant phenotype from the constitutive expression of a broad-substrate esterase. Whether this is due to targeting of the esterase to the ER or the lack of esterase activity against plant endogenous substrates is not clear. A second interesting observation is the lack of plant endogenous esterase activity against the pyridine herbicides. It has been reported that plants contain multiple esterases (Krell et al., 1984; Nourse et al., 1989; Brown et al., 1990); however it is not clear why they are not active on pyridine esters or their precise role in xenobiotic metabolism.

Transformed Plant Cells and Transgenic Plants

A DNA molecule of the present invention can be inserted into the genome of a plant by any suitable method. Suitable plant transformation methods include Agrobacterium-mediated transformation, the use of liposomes, electroporation, chemicals that increase free DNA uptake, free DNA delivery via microprojectile bombardment, transformation using viruses or pollen, etc.

After transformation of cells (or protoplasts), choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, rapeseed, etc.), Cucurbitaceae (melons and cucumber), Graminae (wheat, rice, corn, etc.), Solanaceae (potato, tobacco, tomato, peppers), etc.

Such methods of plant transformation and regeneration are well known to the skilled individual (for example, see Hinchee et al. (1994), and Ritchie & Hodges (1993) for reviews).

A plant transformed with an expression vector containing a pyridine esterase gene of the present invention is also contemplated. A transgenic plant derived from such a transformed or transgenic cell is also contemplated. Those skilled in the art will recognize that a chimeric plant gene containing a structural coding sequence of the present invention can be inserted into the genome of a plant by methods well known in the art. Such methods for DNA transformation of plant cells include Agrobacterium-mediated plant transformation, the use of liposomes, transformation using viruses or pollen, electroporation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as infection by *A. tumefaciens* and related Agrobacterium strains, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like. Microprojectile bombardment and electroporation are particularly effective in methods designed for effecting mitochondrial, chloroplast, or plastid DNA transformation.

Technology for introduction of DNA into cells is well-known to those of skill in the art. Four general methods for delivering a gene into cells have been described: (1) chemical methods (Graham and van der Eb, 1973); (2) physical methods such as microinjection (Capecchi, 1980), electroporation (Wong and Neumann, 1982; Fromm et al., 1985) and the gene gun (Johnston and Tang, 1994; Fynan et al., 1993); (3) viral vectors (Clapp, 1993; Lu et al., 1993; Eglitis and Anderson, 1988a; 1988b); and (4) receptor-mediated mechanisms (Curiel et al., 1991; 1992; Wagner et al., 1992).

Electroporation

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation is well-known to those of skill in the art. To effect transformation by electroporation, one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner, rendering the cells more susceptible to transformation. Such cells would then be recipient to DNA transfer by electroporation, which may be carried out at this stage, and transformed cells then identified by a suitable selection or screening protocol dependent on the nature of the newly incorporated DNA.

Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like. Using these particles, DNA is carried through the cell wall and into the cytoplasm on the surface of small metal particles as described (Klein et al., 1987; Klein et al., 1988; Kawata et al., 1988). The metal particles penetrate through several layers of cells and thus allow the transformation of cells within tissue explants. The microprojectile bombardment method is preferred for the identification of chloroplast or plastid directed transformation events.

An advantage of microprojectile bombardment, in addition to it being an effective means of reproducibly and stably transforming plant cells, is that neither the isolation of protoplasts (Cristou et al., 1988) nor the susceptibility to Agrobacterium infection is required. An illustrative embodiment of a method for delivering DNA into plant cells by acceleration is a Biolistics Particle Delivery System (Brown et al., U.S. Pat. No. 5,424,412; 1995), which can be used to propel particles coated with DNA or cells through a screen, such as a stainless steel or NYTEX™ screen, onto a filter surface covered with the plant cultured cells in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature plant embryos.

Accordingly, it is contemplated that one may desire to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

The methods of particle-mediated transformation is well-known to those of skill in the art. U.S. Pat. No. 5,015,580 (specifically incorporated herein by reference) describes the transformation of soybeans using such a technique.

Arobacterium-Mediated Transfer

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described (Fraley et al., 1985; Rogers et al., 1987). The genetic engineering of cotton plants using Agrobacterium-mediated transfer is described in U.S. Pat. No. 5,004,863 (specifically incorporated herein by reference); like transformation of lettuce plants is described in U.S. Pat. No. 5,349,124 (specifically incorporated herein by reference); and the Agrobacterium-mediated transformation of soybean is described in U.S. Pat. No. 5,416,011 (specifically incorporated herein by reference). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern Agrobacterium transformation vectors are capable of replication in *E. coli* as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant varieties where Agrobacterium-mediated transformation is efficient, it is the method of choice because of the facile and defined nature of the gene transfer.

Agrobacterium-mediated transformation of leaf disks and other tissues such as cotyledons and hypocotyls appears to be limited to plants that Agrobacterium naturally infects. Agrobacterium-mediated transformation is most efficient in dicotyledonous plants. Few monocots appear to be natural hosts for Agrobacterium, although transgenic plants have been produced in asparagus using Agrobacterium vectors as described (Bytebier et al., 1987). Other monocots recently have also been transformed with Agrobacterium. Included in this group are corn (Ishida et al.) and rice (Cheng et al.).

A transgenic plant formed using Agrobacterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

An independent segregant may be preferred when the plant is commercialized as a hybrid, such as corn. In this case, an independent segregant containing the gene is crossed with another plant, to form a hybrid plant that is heterozygous for the gene of interest.

An alternate preference is for a transgenic plant that is homozygous for the added structural gene; i.e. a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for gene of interest activity and mendelian inheritance indicating homozygosity relative to a control (native, non-transgenic) or an independent segregant transgenic plant.

Two different transgenic plants can be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments (see e.g., Potrykus et al., 1985; Lorz et al., 1985; Fromm et al., 1985; Uchimiya et al., 1986; Callis et al., 1987; Marcotte et al., 1988).

Application of these systems to different plant germplasm depends upon the ability to regenerate that particular plant variety from protoplasts. Illustrative methods for the regeneration of cereals from protoplasts are described (see, e.g., Fujimura et al., 1985; Toriyama et al., 1986; Yamada et al., 1986; Abdullah et al., 1986).

Methods for introducing DNA into intact cells or tissues can be utilized to transform plant germplasm that cannot be successfully regenerated from protoplasts. For example, regeneration of cereals from immature embryos or explants can be effected as described (Vasil et al., 1989).

Gene Expression in Plants

Unmodified bacterial genes are often poorly expressed in transgenic plant cells. Plant codon usage more closely resembles that of humans and other higher organisms than unicellular organisms, such as bacteria. Several reports have disclosed methods for improving expression of recombinant genes in plants (Murray et al., 1989; Diehn et al., 1996; Iannacone et al., 1997; Rouwendal et al., 1997; Futterer et al., 1997; and Futterer and Hohn, 1996). These reports disclose various methods for engineering coding sequences to represent sequences which are more efficiently translated based on plant codon frequency tables, improvements in codon third base position bias, using recombinant sequences which avoid suspect polyadenylation or A/T rich domains or intron splicing consensus sequences. While these methods for synthetic gene construction are notable, synthetic genes of the present invention were prepared according to the method of Brown et al. (U.S. Pat. No. 5,689,052; 1997), which is herein incorporated in its entirety by reference. Thus, the present invention provides a method for preparing synthetic plant genes express in planta a desired protein product at levels significantly higher than the wild-type genes. Briefly, according to Brown et al., the frequency of rare and semi-rare monocotyledonous codons in a polynucleotide sequence encoding a desired protein are reduced and replaced with more preferred monocotyledonous codons. Enhanced accumulation of a desired polypeptide encoded by a modified polynucleotide sequence in a monocotyledonous plant is the result of increasing the frequency of preferred codons by analyzing the coding sequence in successive six nucleotide fragments and altering the sequence based on the frequency of appearance of the six-mers as to the frequency of appearance of the rarest 284, 484, and 664 six-mers in monocotyledonous plants. Furthermore, Brown et al. disclose the enhanced expression of a recombinant gene by applying the method for reducing the frequency of rare codons with methods for reducing the occurrence of polyadenylation signals and intron splice sites in the nucleotide sequence, removing self-complementary sequences in the nucleotide sequence and replacing such sequences with nonself-complementary nucleotides while maintaining a structural gene encoding the polypeptide, and reducing the frequency of occurrence of 5'-CG-3' dinucleotide pairs in the nucleotide sequence. These steps are performed sequentially and have a cumulative effect resulting in a nucleotide sequence containing a preferential utilization of the more-preferred monocotyledonous codons for monocotyledonous plants for a majority of the amino acids present in the desired polypeptide. U.S. Pat. No. 5,500,365 (specifically incorporated herein by reference) describes a method for synthesizing plant genes to optimize the expression level of the protein for which the synthesized gene encodes. This method relates to the modification of the structural gene sequences of the exogenous transgene, to make them more "plant-like" and therefore more likely to be translated and expressed by the plant, monocot or dicot. However, the method as disclosed in U.S. Pat. No. 5,689,052 provides for enhanced expression of transgenes, preferably in monocotyledonous plants.

DNA can also be introduced into plants by direct DNA transfer into pollen as described (Zhou et al., 1983; Hess, 1987). Expression of polypeptide coding genes can be obtained by injection of the DNA into reproductive organs of a plant as described (Pena et al., 1987). DNA can also be injected directly into the cells of immature embryos and the rehydration of desiccated embryos as described (Neuhaus et al., 1987; Benbrook et al., 1986).

By transforming plants using transformation methods such as those disclosed herein, the amount of a gene coding for a polypeptide of interest (i.e. a gene encoding a pyridine resistance enzyme or protein, which is equivalent to a pyridine herbicide tolerance gene or a pyridine herbicide selectable marker) can be increased in plants. In particular, chloroplast or plastid transformation can result in desired coding sequences being present in up to about 10,000 copies per cell in tissues containing these subcellular organelle structures (McBride et al., 1995).

Selection of Transformed Cells

After effecting delivery of exogenous DNA to recipient cells, the next step to obtain a transgenic plant generally concern identifying the transformed cells for further culturing and plant regeneration. As mentioned herein, in order to improve the ability to identify transformants, one may desire to employ a selectable or screenable marker gene as, or in addition to, the expressible gene of interest. In this case, one would then generally assay the potentially transformed cell population by exposing the cells to a selective agent or agents, or one would screen the cells for the desired marker gene trait.

An exemplary embodiment of methods for identifying transformed cells involves exposing the transformed cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing. One example of a preferred marker gene confers resistance to glyphosate. When this gene is used as a selectable marker, the putatively transformed cell culture is treated with glyphosate. Upon treatment, transgenic cells will be available for further culturing while sensitive, or non-transformed cells, will not. This method is described in detail in U.S. Pat. No. 5,569,834, which is specifically incorporated herein by reference. Another example of a preferred selectable marker system is the neomycin phosphotransferase (nptII) resistance system by which resistance to the antibiotic kanamycin is conferred, as described in U.S. Pat. No. 5,569,834 (specifically incorporated herein by reference). Again, after transformation with this system, transformed cells will be available for further culturing upon treatment with kanamycin, while non-transformed cells will not. Yet another preferred selectable marker system involves the use of a gene construct conferring resistance to paromomycin. Use of this type of a selectable marker system is described in U.S. Pat. No. 5,424,412 (specifically incorporated herein by reference). Yet the most preferable selectable marker system would take advantage of the genes disclosed herein which encode esterases capable of neutralizing the phytotoxic effects of pyridine herbicides, thus providing a novel and unexpected selection for plants, plant cells and other cell types transformed by and expressing esterase from such genes. Such other cell types are not limited to plant cells, but also are envisioned to include bacterial, fungal, and most other eukaryotic cell types. Selection for such esterase gene expressing transformed cell types provides a growth advantage for transformed cells over non-transformed cells when exposed to, for plants for example, phytotoxic levels of pyridines, and for non-plant cell types for example, biologically detrimental or physiologically unacceptable or growth inhibitory levels of pyridine compounds.

Transplastonomic selection (selection of plastid or chloroplast transformation events) is simplified by taking advantage of the sensitivity of chloroplasts or plastids to spectinomycin, an inhibitor of plastid or chloroplast protein synthesis, but not of protein synthesis by the nuclear genome encoded cytoplasmic ribosomes. Spectinomycin prevents the accumulation of chloroplast proteins required for photosynthesis and so spectinomycin resistant transformed plant cells may be distinguished on the basis of their difference in color: the resistant, transformed cells are green, whereas the sensitive cells are white, due to inhibition of plastid-protein synthesis. Transformation of chloroplasts or plastids with a suitable bacterial aad gene, or with a gene encoding a spectinomycin resistant plastid or chloroplast functional ribosomal RNA provides a means for selection and maintenance of transplastonomic events (Maliga, 1993).

It is further contemplated that combinations of screenable and selectable markers will be useful for identification of transformed cells. In some cell or tissue types a selection agent, such as glyphosate or kanamycin, may either not provide enough killing activity to clearly recognize transformed cells or may cause substantial nonselective inhibition of transformants and non-transformants alike, thus causing the selection technique to not be effective. It is proposed that selection with a growth inhibiting compound, such as glyphosate at concentrations below those that cause 100% inhibition followed by screening of growing tissue for expression of a screenable marker gene such as kanamycin would allow one to recover transformants from cell or tissue types that are not amenable to selection alone. Combinations of selection and screening may enable one to identify transformants in a wider variety of cell and tissue types. Preferred selection combinations include a glyphosate plus an esterase composition, or a phosphotransferase plus an esterase composition. A composition combining two or more selectable markers is also a contemplated, particularly for plants which are to be field selected on the basis of a transposable or excisable element which contains one or more of the selectable markers in a transformed plant, such that the selectable markers can be removed from plant lines which are believed to be best suited for commercialization. Such excisable or transposable elements which function for this particular purpose in plant systems are described in Oliver et al., U.S. Pat. No. 5,723,765 (1998).

Regeneration of Transformants

The development or regeneration of plants from either single plant protoplasts or various explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by Agrobacterium from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983). In particular, U.S. Pat. No. 5,349,124 (specification incorporated herein by reference) details the creation of genetically transformed lettuce cells and plants resulting therefrom which express hybrid crystal proteins conferring insecticidal activity against Lepidopteran larvae to such plants.

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, or pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A preferred transgenic plant is an independent segregant and can transmit the esterase gene and its activity to its progeny. A more preferred transgenic plant is homozygous for the gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for increased expression of the esterase transgene.

The features of the resistance attainable through practice of this invention can be optimized, for example by targeting expression to specific tissues, by temporal expression during early germination when thiazopyr exposure is high, etc.

The following examples are included to demonstrate preferred embodiments of the invention. It should be appreciated by those of skill in the art that the techniques disclosed in the examples which follow represent those discovered to function well in the practice of the invention, and thus can be considered to constitute examples of preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Materials and Methods

Materials. Radiolabeled substrates were all provided by the radiosynthesis group in Monsanto Co. The specific activity of [4-$^{14}$C]pyridine-labeled thiazopyr ([$^{14}$C] thiazopyr) was 27.97 mCi/mmol, and was determined by HPLC to be >99% pure. The specific activity of [4-$^{14}$C] pyridine-labeled MON 14300 ([$^{14}$C]MON 14300) was 27.96 mCi/mmol, and was determined by HPLC to be >98% pure. The specific activity of [$^{14}$C]pyrazole-labeled halosulfuron (a sulfonylurea herbicide containing a methylester group) was 19.30 mCi/mmol, and was determined by HPLC to be >98% pure. Halosulfuron was used as an example of a methyl-ester containing but non-pyridine herbicide. Esterase substrates (p-nitrophenyl butyrate, 4-methyl umbelliferyl butyrate and 5-bromo-4-chloro-3-indolyl acetate) as well as liver esterases (carboxyl esterase; carboxylic-ester hydrolase; EC 3.1.1.1) from porcine and rabbit were obtained from Sigma Chem. Co.

Esterase activity assays. Esterase activity was measured in vitro by conversion of either [$^{14}$C]thiazopyr or [$^{14}$C]MON 14300 to their corresponding monoacid. Pyridine-esterase activity was assayed during protein purification and from tissue extracts of transgenic plants. The homogenizing buffer for plant tissues consisted of 100 mM Tris pH 8.0, 1 mM EDTA, 1 mM DTT, and 10% glycerol in water. Plant tissues (1 g/ml buffer) including leaves, seeds, flowers, seedlings, etc. were homogenized in conical centrifuge tubes using a spinning pestle at 4° C. Following centrifugation (12,000× g), the supernatant (250 μl) was assayed immediately for esterase activity by incubation with [$^{14}$C]thiazopyr or [$^{14}$C]MON 14300 (4 μg) in 0.1 M Tris pH 8.0 buffer (50 μl) at 37° C. The reaction was sampled (100 μL) at various times (0.5 to 100 hr) to generate a kinetic profile of monoacid formation. The reaction was stopped by addition of 1% trifluoroacetic acid in acetonitrile (v/v, 150 μl). Following centrifugation (12,000× g for 3 min), the supernatant was analyzed by HPLC/RAD (radioactivity detection) to resolve the monoacid from the parent herbicide and other metabolites. Control reactions in the absence of the esterase recovered un-reacted thiazopyr or MON 14300 for the duration of experiments. Esterase activity was also assayed during protein purification following a similar procedure except a single time-point (1–2 hrs) of incubation was selected within the linear range of reaction. In vitro assays also employed three commonly used calorimetric (p-nitrophenyl butyrate) or fluorescent (4-methyl umbelliferyl butyrate and 5-bromo-4-chloro-3-indolyl acetate) substrates. These substrates are useful in rapidly and qualitatively detecting general esterase activity.

Esterase activity was also monitored in plants. [$^{14}$C] Thiazopyr or [$^{14}$C]MON 14300 (1–4 μg in acetonitrile) was applied directly to shoots and cotyledons of young seedlings. After 2 days in a growth chamber, tobacco or tomato seedlings were washed with methanol and water, then homogenized (TISSUMIZER™, Tekmar-Dohrmann, Cincinnatti, Ohio) in 5% (v/v) trifluoroacetic acid in acetonitrile (fresh w/v ratio of 2/1). Homogenates were clarified by centrifugation (12,000× g) and supernatants analyzed by HPLC/RAD for the formation of the monoacid metabolite.

HPLC/RAD analysis. Three individual HPLC methods were employed for separating the corresponding monoacid metabolites of thiazopyr, MON 14300 or halosulfuron. A reverse-phase Beckman ULTRASPHERE™ column (4.6× 25 mm) was employed in the separation of thiazopyr monoacid. The solvents consisted of methanol and 0.2% (v/v) trifluoroacetic acid in water at a flow rate of 1 ml/min. The gradient program consisted of 60% methanol for 12 min; 60 to 75% methanol in 8 min hyperbolic curve 5; 75% for 6 min, 75 to 100% methanol linearly in 1 min, and 100% for 4 min. The effluent was analyzed in series by UV (254 nm) and by a radioactivity flow detector (Packard TRACE II™, homogeneous cell with ATOMLIGHT™ cocktail at 3 ml/min). Under this gradient program, thiazopyr monoacid eluted at 16.0 min.

For MON 14300 monoacid, a reverse-phase Waters μBONDAPAK™ column (4.6×25 mm) was employed. The solvents consisted of acetonitrile and 0.2% trifluoroacetic acid in water at a flow rate of 1 ml/min. The gradient program consisted of 50 to 80% acetonitrile linearly in 5 min; 80% acetonitrile for 5 min; 80 to 100% acetonitrile linearly in 1 min, and 100% acetonitrile for 4 min. Under this gradient program, MON 14300 monoacid eluted at 12.0 min.

For halosulfuron monoacid, a reverse-phase Beckman ULTRASPHERE column (4.6×25 mm) was employed. The solvents consisted of acetonitrile and 0.2% trifluoroacetic acid in water at a flow rate of 1 ml/min. The gradient program consisted of 20 to 100% acetonitrile linearly in 15 min; 100% acetonitrile for 4 min. Under this gradient program, halosulfuron monoacid eluted at 15.3 min.

Example 1

Purification of pyridine-esterases from porcine and rabbit liver. Porcine and rabbit liver esterases, obtained commercially as $(NH_4)_2SO_4$ suspensions, were desalted using a disposable SEPHADEX™ G25 size exclusion column (Pharmacia Biotech). Proteins (1 to 10 mg) were initially separated on a strong anion exchange column (MONO Q™, Pharmacia Biotech) at 4° C. The column was linearly programmed in 30 minutes from 0 to 0.4 M KCl in 10 mM Tris buffer, pH 7.4 at a flow rate of 1 m/min. Subsequently, the column was programmed from 0.4 to 1.0 M KCl in 10 min. Effluent was monitored by UV (280 nm) and fractions were collected at 1 ml intervals. Effluent fractions were assayed for protein by Coomassie dye (Bio Rad Laboratory) and for pyridine-esterase activity. Protein purity was determined by SDS-PAGE on 10 to 15% gradient gels (Pharmacia Biotech) with visualization of proteins by silver staining.

Following anion exchange chromatography, fractions with the highest purity and activity were pooled. After desalting, the pooled fractions were further separated by isoelectric focusing (IEF) chromatography on a MONO P™ column (Pharmacia Biotech) at 4° C. IEF chromotography was conducted at different pH ranges (3–9, 4–7, 5.5–6.5 or 4.5–5.5) using appropriate combinations of POLY-BUFFERS™ (Pharmacia Biotech) and a flow rate of 0.5 m/min. Effluent fractions from IEF chromatography were analyzed for protein and pyridine-esterase activity. The protein purity of the fractions was determined by SDS-PAGE and IEF-PAGE.

The commercially available preparations of porcine liver esterase demonstrated activity against thiazopyr, MON 14300, and standard esterase substrates. MON 14300 not only was hydrolyzed faster than thiazopyr, but also had the advantage of undergoing little to no metabolism in plants which facilitated chromatographic separation of the monoacid metabolite. Because of these advantages, we employed MON 14300 as the substrate of choice for assaying esterase activity. Since thiazopyr represents an herbicide of interest, we also monitored esterase activity against thiazopyr.

SDS-PAGE analysis of the commercial porcine esterase preparation showed one major band with an apparent molecular weight of 60 kD and approximately six minor bands. This preparation was desalted and was resolved using anion exchange chromatography into one major peak. Fractions collected from the major peak demonstrated a single 60 kD protein and pyridine-esterase activity. IEF-PAGE (pH 3–9, and 4–6.5) analysis of the 60 kD esterase showed a smear of bands centered around pI 5.0 suggesting the presence of numerous isozyme species which are commonly reported with liver esterases (Long, et al., 1988; (Kao et al., 1985); (Mentlein et al., 1980). The most active fractions from the anion exchange purification were pooled, desalted, and further purified by IEF chromatography (pH 4.5–5.5). The protein profile indicated that there were five closely eluting peaks each demonstrating esterase activity. The most active fractions were analyzed by IEF-PAGE (pH4.5 to 5.5) which showed varying amounts of three major isozymes at pI 5.0. One fraction containing one major and two minor isozymes was submitted for N-terminal amino acid sequencing. A single sequence of 15 amino acids was obtained from the N-terminus (Table 1) with good protein recovery. Kinetic constants of the purified porcine esterase against thiazopyr demonstrated a Vmax of 10.8 nmol/min/mg and a Km of 0.32 mM as calculated from the double reciprocal plot analysis ($R^2$=0.999).

The commercially available rabbit liver esterase was also active against MON 14300 and thiazopyr. SDS-PAGE analysis of the preparation showed numerous proteins including two at 60 kD molecular mass. Anion exchange chromatography resolved the rabbit liver esterase into a doublet protein peak; the majority of the thiazopyr activity as well as a 60 kD protein resided in the later eluting peak. The most active fractions from the anion exchange chromatography were pooled, desalted, and subjected to a second round of anion exchange chromatography. SDS-PAGE analysis of the active fractions from the second anion exchange chromatography showed one band with a molecular mass of 60 kD. IEF-PAGE analysis of the 60 kD esterase once again resolved into a smear of bands centered around pI 6.0. The most active fractions from the second anion exchange chromatography were pooled, desalted, and further purified by IEF chromatography (pH 5.5–6.5). Major and minor protein peaks were resolved with both peaks demonstrating thiazopyr esterase activity. Analysis of the major protein peak by IEF-PAGE (pH 4–6.5) showed two major isozymes with a pI 6.0. A fraction containing the two isozymes was sequenced yielding one N-terminal sequence for 20 amino acids with good recovery of proteins. Kinetic constants of the purified rabbit esterase against thiazopyr demonstrated a Vmax of 6.63 nmol/min/mg and a Km of 0.019 mM as calculated from the double reciprocal plot analysis ($R^2$ 0.996).

The N-terminus amino acid sequences of rabbit and porcine pyridine-esterases were compared against databases for homology. No significant homology was found with the porcine esterase; however, high homology was found between the rabbit pyridine-esterase and a published esterase isozyme 1 of rabbit liver (RLE1) (Korza, et al., 1988) with identity in seventeen of the eighteen N-terminus residues (Table 1). RLE1 and rabbit pyridine-esterase shared an identical pI (6.0), molecular mass (60 kD) and a nearly identical N-terminal

TABLE 1

Comparison of N-terminal amino acid sequence of the purified liver esterase from rabbit (RLE3) and porcine with the published rabbit esterase isozyme 1 (RLE1).

| Residue | Purified rabbit liver esterase (RLE3) | Published rabbit liver esterase (RLE1) | Purified porcine liver esterase |
|---|---|---|---|
| 1 | X | HIS | X |
| 2 | PRO | PRO | (GLU) |
| 3 | X | SER | (PRO) |
| 4 | ALA | ALA | ALA |
| 5 | PRO | PRO | (SER/ALA) |
| 6 | PRO | PRO | PRO |
| 7 | VAL | VAL | PRO |
| 8 | VAL | VAL | VAL |
| 9 | ASP | ASP | VAL |

TABLE 1-continued

Comparison of N-terminal amino acid sequence of the purified liver esterase from rabbit (RLE3) and porcine with the published rabbit esterase isozyme 1 (RLE1).

| Residue | Purified rabbit liver esterase (RLE3) | Published rabbit liver esterase (RLE1) | Purified porcine liver esterase |
|---|---|---|---|
| 10 | THR | THR | ASN |
| 11 | VAL | VAL | THR |
| 12 | HIS | LYS | ALA |
| 13 | GLY | GLY | GLU |
| 14 | LYS | LYS | X |
| 15 | VAL | VAL | (ARG/GLY) |
| 16 | LEU | LEU | |
| 17 | GLY | GLY | |
| 18 | LYS | LYS | |
| 19 | PHE | PHE | |
| 20 | VAL | VAL | | sequence. A second isozyme (RLE2) of rabbit liver esterase has also been published (Ozols, 1989) which did not show homology to the purified pyridine-esterase. Preparations of the RLE1 and RLE2 were provided by Professor J. Ozols (Univeristy of Connecticut). Thiazopyr hydrolytic activity could be demonstrated with RLE1 but not with RLE2 suggesting that the purified rabbit pyridine-esterase was in fact RLE1.

Example 2

PCR cloning of a rabbit liver esterase cDNA. Based on the published amino acid sequence of rabbit liver esterase isozyme 1 (RLE1) (Ozols, 1987), we designed 64-fold degenerate primers at the amino and carboxy termini of the mature protein utilizing nucleotide degeneracy only in the 3' region of the primer. The amino terminal primer contained an Nco I restriction site encoding an initiating methionine residue for expression. The carboxy terminal contained a termination codon and the restriction sites Xba I and Sac I for cloning. The primer for the amino terminal (SEQ ID NO:4) was 5'-GCACCATGGC CCACCCCTCC GCAC-CACCTG TGGTTGACAC TGTNAARGGN AARGT-3' and the primer for the carboxy terminal (SEQ ID NO:5) was 5'-CGCTCTAGAG CTCTACAGYT CGATRTGYTC NGTYTC-3'.

Rabbit liver poly A+RNA (2 μg) was reacted with AMV reverse transcriptase according to the manufacturer's instructions to generate first strand cDNA for use as template in the PCR™ reaction. An equivalent of 80 ng of starting material was used for 30 cycles of PCR™ with Taq polymerase in segments of 94° C. (1 min), 25° C. (2 min) and 72° C. (2 min). Products in the 1300 to 1900 base pair range were recovered and reamplified as above with an annealing temperature of 35° C. The reaction yielded a single band, approximately 1700 base pairs, which was the predicted molecular weight for a sequence encoding an esterase of about 60 k Da. The predicted esterase clone was completely sequenced in both directions utilizing the Sanger method and the SEQUENASE™ reagents (US Biochemical). The deduced amino acid sequence from the cloned esterase encoding cDNA showed divergence from the published RLE1 and was designated as isozyme 3 (RLE3).

A synthetic endoplasmic reticulum (ER) signal sequence was designed based on a published homologous esterase cDNA sequence (Robbi et al., 1990). Oligonucleotides of 56 (SEQ ID NO:6) and 57 (SEQ ID NO:7) nucleotides were synthesized to encode both strands of the signal sequence. An alanine codon was added downstream of the initiating methionine codon in order to incorporate an Nco I restriction site.

Unexpectedly, sequence analysis of the recovered cDNA indicated that it encoded an esterase which was different from the published sequence for RLE1. The derived amino acid sequence of the new clone was 95% homologous to RLE1 with most of the divergence lying in one region of the clone (see FIG. 2). Other than this region, only three amino acid residues in the clone differed from RLE1. Interestingly, the divergent sequence in the clone was homologous to a portion of the published sequence in RLE2 (Ozols, 1989). Other subclones isolated from the PCR amplification were sequenced through this divergent region and were all identical to the original clone. The RLE3 clone encoded a novel esterase. Comparison of the sequence of RLE3 with other published sequences revealed a highly homologous clone isolated from the rat (Robbi et al., 1990).

Example 3

Construction of a cDNA for RLE1. Using the cloned RLE3 cDNA as the template, we carried out two independent PCR events to generate a cDNA for RLE1. Two oligonucleotides were designed such that the 3' end was homologous to RLE3 sequences flanking the divergent region, and the 5' end encoding the divergent region of RLE1. The two primers, (SEQ ID NO:8) (SEQ ID NO:9) were designed with opposite orientations and contained an overlapping segment in the RLE1 divergent region along with a unique ClaI restriction site. Two PCR reactions were run independently utilizing RLE3 cDNA as the template, producing two double stranded DNAs encoding for two halves of RLE1. The double-stranded DNAs were recovered into pBluescript (Stratagene, La Jolla, Calif.), each clipped at one end with ClaI, and assembled by blunt-end ligation.

Since a purified preparation of RLE1 esterase from Prof. Ozols demonstrated thiazopyr hydrolysis, we proceeded to construct a cDNA for RLE1. Conversion of this cDNA to RLE1 was completed by site specific mutagenesis at three other positions using mutagenesis oligonucleotides herein designated as (SEQ ID NO:10) and (SEQ ID NO:11). These oligonucleotides function to alter Gln71 to serine, Leu309 to tyrosine, and Ala310 to glutamate at positions where only single amino acid differences existed between RLE1 and RLE3. The entire sequence of the RLE1 cDNA was confirmed by double stranded nucleic acid sequencing.

Example 4

Expression of RLE1 and RLE3 cDNAs in insect cells. Mature rabbit liver esterases are glycoproteins which reside in the lumen of the endoplasmic reticulum (ER) (Korza et al., 1988). The cloning strategy that recovered RLE3 cDNA was based on the amino acid sequence of the RLE1 mature protein which did not contain a signal sequence for ER targeting. Assuming that glycosylation and/or disulfide bond formation in the ER is critical to esterase activity, an ER signal sequence was designed based on the published oligonucleotide sequence of the rat liver esterase (Robbi et al., 1990). A standard baculovirus mediated insect expression system was employed utilizing a transfer vector (pVL1893) with an AcNPV polyhedrin promoter. Transfer vector DNA (2 µg) containing the esterase gene along with 1 µg of baculovirus genomic DNA was transfected into *Spodoptera frugiperda* clone 9 (SF9) cells by the standard calcium phosphate method. 5 days after transfection, cells were collected by centrifugation at 3000× g. The cell free supernatant and the cell lysate were tested for esterase activity against thiazopyr and MON 14300, and for the 60 kD esterase protein by Western blot analysis. Recombinant baculovirus clones containing the esterase genes were identified by dot blot DNA hybridization and purified by three rounds of plaque purification. Control experiments demonstrated no esterase activity in the blank media, SF9 cells or SF9 cells infected with wild type baculovirus. All baculovirus expression methods were accomplished according to O'Reilly et al., 1992.

The culture media from cells containing the RLE3 cDNA demonstrated esterase activity against standard substrates, thiazopyr and MON 14300. The esterase activity was inactivated by boiling, and also by bis(p-nitropheyl) phosphate, a previously demonstrated esterase inhibitor. Surprisingly, the culture media from the RLE1 cells were inactive against all esterase substrates. Western blot analysis using antibodies against the pyridine-esterase detected high levels of the 60 kD esterase protein in the media of both RLE1 and RLE3 cultures. The recombinant insect cells from RLE 1 and RLE3 were purified by three successive rounds of plaque purification. Analysis of cell lysates from RLE1 and RLE3 for esterase activity and protein produced similar results as the media. These results demonstrated that although both RLE1 and RLE3 were equally expressed in insect cells, only RLE3 protein demonstrated esterase activity. The failure of the 60 kD protein product from RLE1 to hydrolyze even standard esterase substrates suggests that the enzyme is non-functional. The inactivity of the RLE1 esterase could be due to lack of proper folding, although RLE3 esterase which is 95% homologous to RLE1 was folded correctly. The absence of activity in the protein product of RLE1 cDNA produced herein and the presence of activity in the purified RLE1 esterase from Prof. Ozols would suggest the likelihood that errors may exist in the published amino acid sequence of RLE1 (Ozols, 1987). The DNA sequence of RLE1 cDNA produced herein was not determined.

Example 5

Stable transformation of RLE3 cDNA was examined in two model plants, tomato and tobacco. The vectors for stable expression in tomato (UC82B) and tobacco (Samson) contained the FMV (figwort mosaic virus) Is promotor and RLE3 esterase cDNA with ER targeting sequence. The vectors also contained the NPTII (neomycin phosphotransferase) gene as the selectable marker.

Prridine-esterase protein levels were analyzed by Western blot assay as described previously (Feng et al., 1995). Briefly, plant tissue extracts were generated using the homogenizing buffer for in vitro activity assays (described above). Proteins in extracts were separated using SDS-PAGE and blotted onto nitrocellulose membrane. The presence of the 60 kD pyridine-esterase protein was detected using antibodies from a goat immunized with purified rabbit liver esterase. Protein assays for the plant extracts employed Coomassie dye.

The plant vector was introduced via Agrobacterium transformation (Horsch et al., 1985), and primary callus tissues were selected for kanamycin resistance. Shoots from the primary calli were rooted and regenerated into $R_0$ plants which were potted in soil and maintained in the greenhouse. A 0.5 cm diameter leaf punch was collected, and tissue extract assayed for the presence of the 60 kD esterase. Expression of the pyridine-esterase was detected in most of the transgenic tobacco lines with expression levels ranging from 0.004 to 0.5% of total protein. Of 35 lines of tomato, 20 lines expressed the esterase at levels ranging from 0.002 to 0.05%. Expression of pyridine-esterase was consistently higher in tobacco than in tomato plants.

In addition to leaves, esterase protein and activity were also detected in tissue extracts from seeds, roots, flowers and fruits; this is consistent with the expression pattern of the constitutive FMV promotor. Since thiazopyr is a pre-emergence herbicide acting primarily during early germination, we were particularly interested in high expression of the pyridine-esterase in young seedlings. Starting with seeds from a high-expressing tobacco line (#37432), we observed consistent expression of the pyridine-esterase through 17-day old seedlings. It is surprising that the ubiquitous expression of the pyridine-esterase in all tissues of plants caused no visible phenotype. Transgenic tobacco and tomato plants were normal in all aspects of development from vegetative growth, flowering, fruit setting and maturation, to seed production and germination. The $R_0$ lines were carried through fruit maturation in order to obtain $R_1$ seeds for resistance assays.

Example 6

Detection of plant esterase activity in vitro and in planta. Activity assays conducted using the leaf extracts from $R_0$ tomato and tobacco plants did demonstrate the hydrolysis of both MON 14300 and thiazopyr with activity being correlated to expression of the 60 kD esterase.

Tissue extracts from 3 tobacco $R_1$ seedlings were employed for further studies. Two of the lines (#37437 and #37432) expressed high levels of esterase (~0.5%) and one line (#37436) which expressed no pyridine-esterase was used as negative control. Tissue extracts were incubated with [$^{14}$C]MON 14300 and formation of the monoacid monitored with time. Results (FIG. 5) showed that the two lines exhibiting high levels of esterase hydrolyzed MON 14300 with first order kinetics to near completion (90% monoacid) within 100 hrs of incubation. In comparison, less that 2% monoacid was detected in line (#37436). These results supported two important conclusions. First, pyridine-esterase was capable of driving the hydrolysis reaction to completion with no apparent product inhibition, and second, there was no endogenous esterase activity in tobacco which catalyzed MON 14300 hydrolysis.

Figure 4:
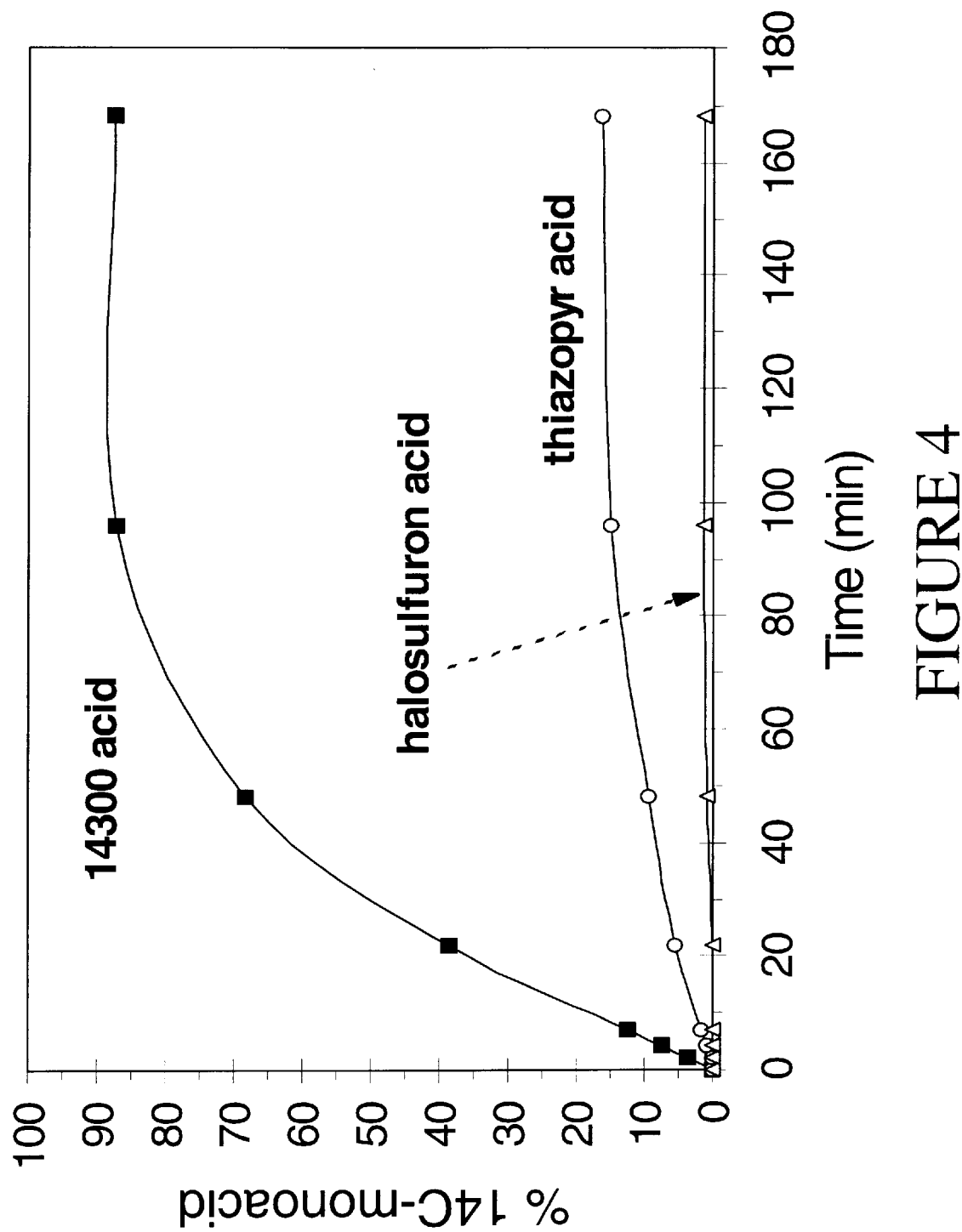
FIG. 4 illustrates the kinetics of pyridine-esterase activity against [$^{14}$C]MON 14300, [$^{14}$C]thiazopyr or [$^{14}$C] halosulfuron (a sulfonylurea herbicide with a methylester group) in extracts from tobacco seedlings (#37437) expressing the pyridine-esterase. Hydrolysis by pyridine-esterase was much faster for MON 14300 than thiazopyr; little to no hydrolysis was detected for halosulfuron.

Another study examined the substrate specificity of the pyridine-esterase in one tobacco line exhibiting high esterase expression levels (#37437) against MON 14300, thiazopyr and halosulfuron (a herbicide of the sulfonylurea family containing a methylester functional group). Results in FIG. 4 demonstrate that pyxidine-esterase clearly hydrolyzed both MON 14300 and thiazopyr, but not halosulfiron. As observed in the crude rabbit esterase preparation, MON 14300 was a better substrate than thiazopyr for the pyxidine-esterase. Dithiopyr, a pyxidine herbicide which contains methyl thioesters, was also not hydrolyzed by the pyridine-esterase. Earlier studies showed that dithiopyr is converted to its monoacid by monooxygenases (Feng et al., 1991).

Figure 5:
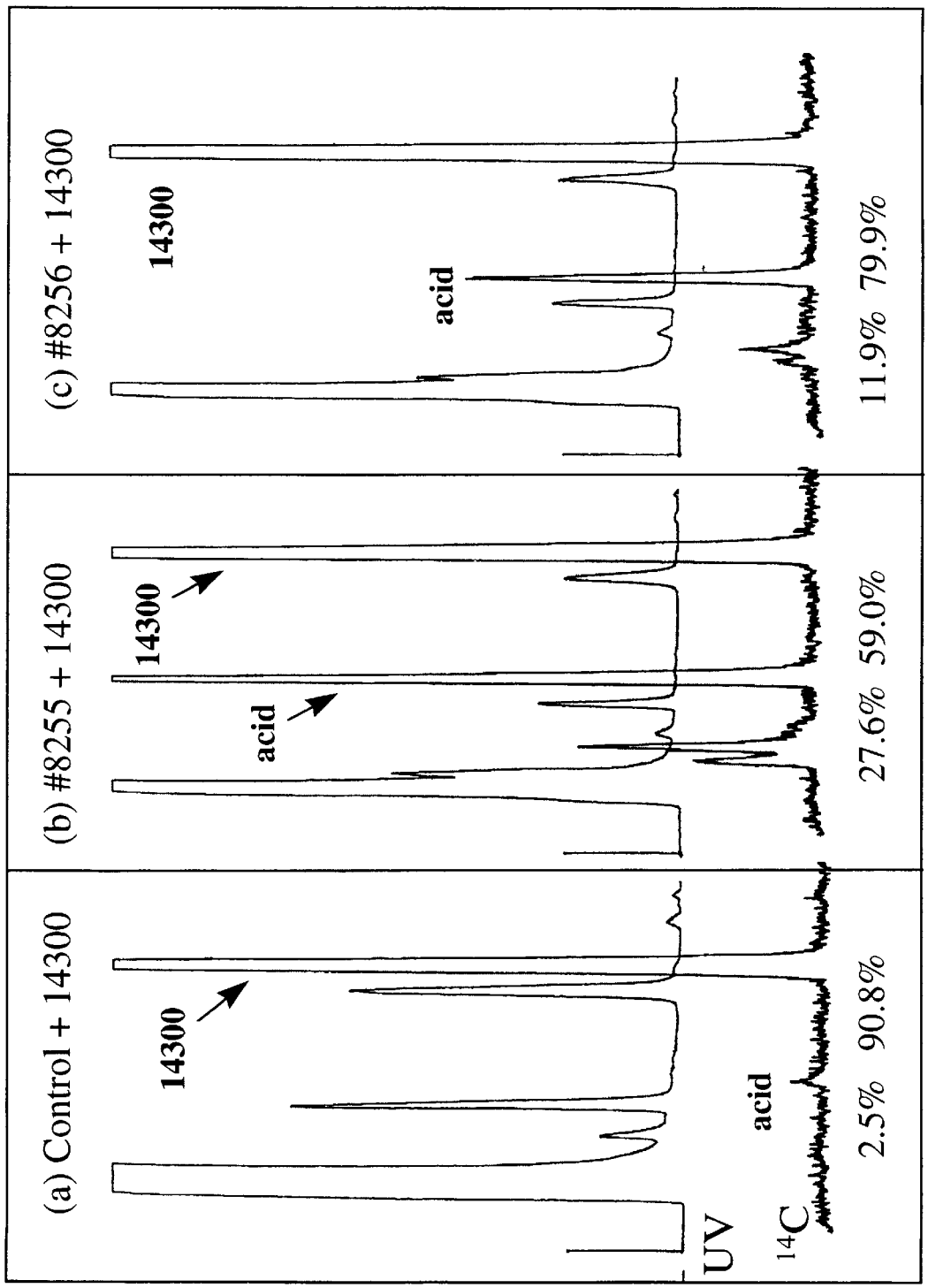
FIG. 5 illustrates in planta metabolism of [$^{14}$C]MON 14300 by control (UC82B, panel a) and transgenic tomato seedlings (#8255, panel b; #8256, panel c). Tissue extracts were analyzed by HPLC with UV$_{254}$ nm (upper trace) and $^{14}$C (lower trace) detection. Only transgenic lines expressing the pyridine-esterase hydrolyzed MON 14300 to the monoacid.

The fact that pyridine-esterase is expressed in plants and shows in vitro activity does not guarantee that thiazopyr, when applied to seedlings, is hydrolyzed. FIG. 5 shows three HPLC profiles illustrating in planta metabolism of MON 14300 in two high expressing tomato lines (#8255 and #8256) and the control (UC82B). MON 14300 was applied to the shoot of 2-day old seedlings. Two days after treatment, seedlings were washed with methanol and tissue extracts analyzed by HPLC. The HPLC chromatograms show signals from both the $UV_{254\ nm}$ (upper trace, FIG. 5) and radioactivity (lower trace, FIG. 5) detectors. For the purpose of metabolite identification, plant extracts were co-injected with a mixture of authentic standards visible under UV detection. Control tomato seedlings (FIG. 5, panel a) showed MON 14300 as the primary residue (90.8%) with little monoacid (2.5%), again demonstrating the lack of endogenous esterase activity against MON 14300. Both transgenic lines (#8255 and #8256) demonstrated rapid conversion of MON 14300 to its monoacid, with line #8255 (FIG. 5, panel b) demonstrating greater activity than #8256 (FIG. 5, panel c). The pyridine-esterase in lines #8255 and #8256 was shown to be 0.05% and 0.005% of the total protein, respectively, which was in agreement with the observed in planta hydrolytic activities. In both transgenic lines, small levels of more polar products, presumably from further degradation of the monoacid as reported by McClanahan et al. (1995), were detected near the solvent front.

Example 7

Root elongation assay for thiazopyr resistance. Transgenic tobacco $R_1$ seeds (line #37432) were sterilized with a 0.25% sodium hypochlorite solution and repeatedly washed with water. Just prior to solidification of agar (~45° C.), stock solutions of thiazopyr in DMSO (1% final concentration) was added; the final concentrations of thiazopyr were 0, 0.05, 0.1, and 0.5 $\mu$M. The liquid agar was vortexed and dispensed (3 ml) into glass test tubes. Seeds (~12 per test tube) were placed on the surface of solidified agar and stored in a growth chamber at 25° C. with a 12 hr day and night cycle. Root development and length were monitored visually with time. Control experiments employed untransformed tobacco seeds from the Samson variety.

Control seedlings were observed to exhibit dose dependent inhibition of root elongation demonstrating about 50% inhibition at 0.1 $\mu$M thiazopyr. In comparison, seedlings from a transgenic line (#37432) expressing the esterase at 0.5% of total protein showed normal root length at 0.1 $\mu$M thiazopyr. Root inhibition was observed at 0.5 $\mu$M thiazopyr in seedlings from transgenic line #37432. These results demonstrate thiazopyr resistance in plants expressing a pyridine-esterase.

Example 8

Growth chamber and greenhouse assay for resistance. Pyridine herbicide resistance in transgenic tomato expressing RLE3 was examined in soil with pre-emergence (PE) applications of thiazopyr. Tomato seeds ($R_1$ of #8255 and #8256, and control UC82B) were planted in 100 cm$^2$ pots (12 seeds per pot) in artificial METROMIX™ soil at a depth of 0.5 cm. Pots were watered and oversprayed with a 50% acetone/water solution (2 ml) containing thiazopyr at use rates of 0, 34, 67, 140, and 280 g/ha (grams per hectare). Pots were placed in a growth chamber (12 hr photoperiod; 60% humidity, 25° C. night/29° C. day; 600 $\mu$E light) with daily watering by subirrigation.

Good germination was observed in all lines, and evidence of resistance was apparent 2–3 weeks later. At 34 g/ha, no detectable difference in vegetative growth was observed between UC82B and #8256. At 67 g/ha, UC82B showed about 20% stunting while #8256 showed none. At 140 g/ha, UC82B never grew beyond the cotyledon stage and eventually all died. In comparison, #8256 showed numerous healthy seedlings that were stunted but otherwise normal when exposed to the 140 g/ha rate. Similar observations were made at the 280 g/ha rate of application. We observed approximately 4 resistant seedlings out of 12 to 16 seeds at the 140 and 280 g/ha treatment rates. The ratio of resistant to sensitive seedlings represented a Mendelian segregation of the pyridine-esterase gene in the $R_1$ generation, and suggests that seeds that are homozygous for the pyridine-esterase gene display the highest levels of resistance, thus the about 1:3 to about 1:4 tolerance to the elevated rates of thiazopyr. Although we observed stunting of the transgenic plants at 140 and 280 g/ha rates, no effect on flower development, fruit set, and seed production were evident. Similar observations were made for the #8255 line.

Example 9

Green house test for tomato resistance. Similar studies were also conducted in greenhouse with pre-plant incorporation (PPI) of thiazopyr into the soil. During pre-emergence application of thiazopyr, it is possible that cracks in soil may allow seedlings to escape from exposure to thiazopyr that was sprayed on the soil surface. One way to prevent such escapes is to apply thiazopyr with pre-plant incorporation (PPI). In this method of application, thiazopyr is first incorporated into the soil and seeds are sowed directly into that soil. PPI application of thiazopyr can cause the most plant injury and therefore require lower rates of thiazopyr application.

Tomato seeds were planted in 100 cm$^2$ pots filled with a sterilized silty loam soil (510 g). Seeds were placed on top of soil, and covered with additional soil (135 g) which was premixed with thiazopyr at equivalent use rates of 0, 34, 45, 67, and 140 g/ha. Greenhouse growing conditions were: 29° C. day to 21° C. night with supplemental lighting as needed to maintain 200–900 $\mu$E.

Figure 6:
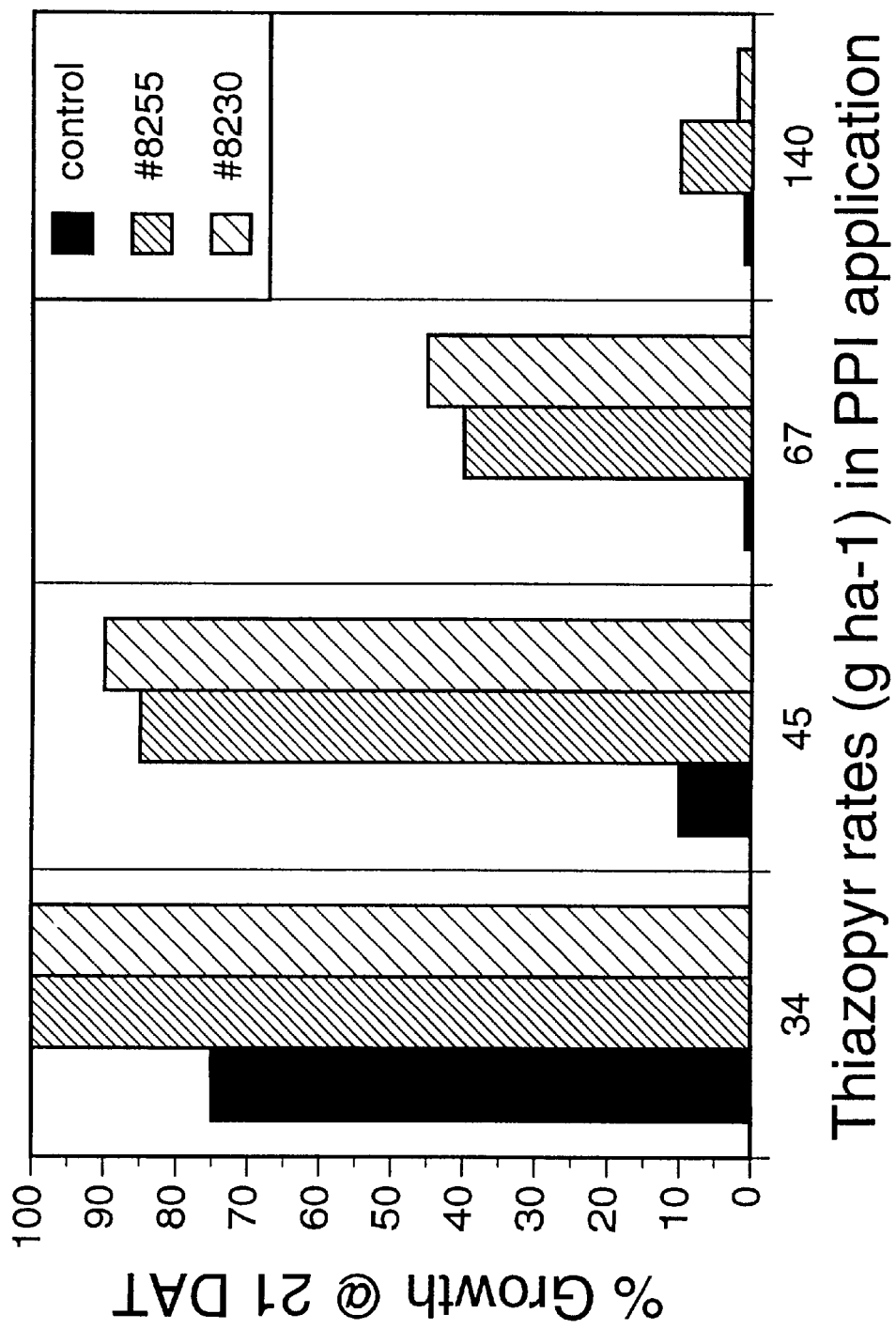
FIG. 6 illustrates the greenhouse demonstration of thiazopyr resistance as measured by % growth in transgenic tomatoes (#8255 and # 8230) at 21 days after treatment. UC82B was the control and thiazopyr was applied with pre-plant incorporation (PPI) at 34, 45, 67 and 140 g/ha.

In order to be certain that tomato resistance to thiazopyr in the above PE experiment was not due to escapes, a further experiment in the greenhouse using conducted using PPI application. Plants were visually rated at 21 days after treatment (DAT) based on comparison of % growth to untreated plants, and the results are presented in the bar chart in FIG. 6. Thiazopyr is considerably more active in the greenhouse than in the field, hence lower use rates were utilized for this test. Results showed that at the 34 g/ha application rate, control line UC82B showed some injury (75% growth) while the two transgenic lines (#8255 and #8230) showed no injury (100% growth). At the 45 g/ha rate, UC82B was severely injured (10% growth) and the transgenics lines minimally injured (90% growth). At the 67 g/ha rate, UC82B plants were dead and the transgenics were stunted at 40 to 50% growth. These results unequivocally demonstrated thiazopyr resistance in tomato plants expressing a pyridine-esterase. Both #8255 and #8230 lines expressed the pyridine-esterase at 0.05% of total protein. The term 'resistance' in all of these examples can also be expressed as a recombinantly acquired tolerance to the applied levels or rates of pyridine herbicide.

Example 10

Field test for tomato resistance. A single field test was conducted in early summer at a Monsanto Company research farm in Jerseyville, Ill. A total of 9 transgenic lines were selected for the field study. Out of these, only 3 lines were demonstrated to be homozygous at the $R_2$ generation (#8255-30, #8255-39, and #8256-39). The remaining 6 lines were $R_1$ seeds selected based on high expression level and seed availability. About 400 seeds were pooled from each line based on uniformity of size and appearance, and randomly separated into 4 groups of about 100 seeds. Four parallel plots (5×20 m) were respectively sprayed with 0, 112, 336, and 673 g/ha of thiazopyr, which was then incorporated down to 7.5 cm of soil depth. The projected field use-rate for thiazopyr is about 280 g/ha. Seeds were placed in a furrow at every 5 cm distance and covered with soil. UC82B seeds were used as untransformed controls. After sowing, 13 mm of water was irrigated over the plots. A combination of late planting date, unusually cool weather, and heavy rain within 24 hours after planting resulted in very poor germination in all plots. Nevertheless, it was possible to measure thiazopyr resistance based on seedling emergence between control UC82B and the transgenic lines. Untreated plots at 21 days after planting showed comparable germination (15 to 20%) between UC82B and #8255-30 (a homozygous expressing line). At 112 g/ha of thiazopyr, both lines showed slightly lower but still comparable germination. However at 336 g/ha, #8255-30 maintained germination at 10% while UC82B declined to about 1%. At 673 g/ha, #8255-30 still showed 4% germination with no germination at all for UC82B. Similar results were observed in other transgenic lines with higher germination being associated with higher expressing homozygous lines. It is estimated that these transgenic tomato lines exhibited pyridine herbicide tolerance at about 1.5 to 2.0× that of the controls at commercial use rates of thiazopyr. Evaluations made at later time points showed that a large proportion of UC82B plants that did manage to germinate at low doses of thiazopyr (112 and 336 g/ha) had died due to weakening of the stem at the soil line from exposure to thiazopyr. Although some of the transgenic lines also showed thiazopyr injury (bulging of the stem near the soil line), their growth was not affected. The transgenic lines flowered, set fruit, and yielded abundant tomatoes and seeds.

Example 11

RLE3 gene as a selectable marker. The RLE3 gene or a substantially similar gene encoding a pyridine esterase have been used as a selectable marker for identifying plant transformation events in which a vector DNA containing the plant expressible gene is included. Such transformed plant cells, transformed by insertion of the gene into the nuclear genome were selected from a population of cells which failed to incorporate a recombinant molecule by growing the cells in the presence of a pyridine herbicide (i.e., Thiazopyr, MON14300, etc). The pyridine herbicide/esterase marker gene combination represents a novel system in tissue culture where only a limited number of selectable markers are available.

Figure 8:
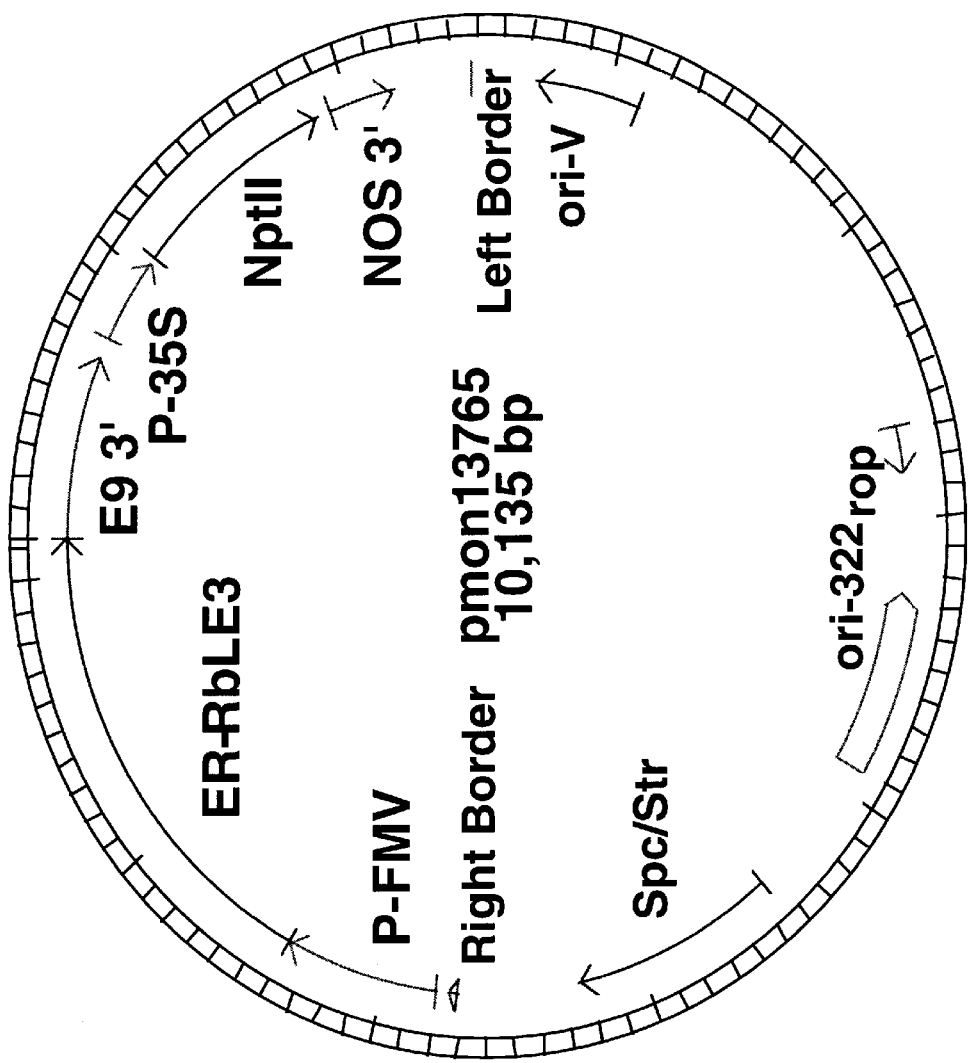
FIG. 8 illustrates plasmid pMON13765, which contains a recombinant RLE3 cDNA coding sequence within a plant expression cassette.

The experimental procedure compared the herbicide toxicity of the pyridines upon exposure to tobacco calli that were transformed with a plasmid DNA, pMON13765 (FIG. 8) containing the RLE3 gene, and tobacco calli controls transformed with isogenic plasmid DNA without the RLE3 gene. The vectors, which also encoded NPTII for kanamycin selection, were introduced via Agrobacterium transformation. Kanamycin resistant calli were cut into pieces of 3–5 mm diameter and transferred onto selection media (Murahige and Skoog basal salt mixture in 0.9% agar) containing 0.01, 0.1, 1.0, or 10.0 $\mu$M concentration of either thiazopyr or MON 14300 (1 mM stock solution in DMSO). Plates were placed in a lighted growth chamber maintained at 22° C. After 2–3 weeks, calli from control vector showed little growth as evidenced by a lack of root or shoot development at pyridine herbicide concentrations above 0.1 $\mu$M. Most control calli were dead after 3 weeks at pyridine herbicide concentrations above 1 $\mu$M. In contrast, calli expressing the RLE3 gene showed vigorous growth and shoot development at 0.1 $\mu$M MON 14300 or thiazopyr. At 1.0 to 10 $\mu$M concentrations, the RLE3 calli showed stunting with reduced shoot development. Preliminary experiments identified 0.1 μM 14300 or thiazopyr as a suitable selection concentration for identifying transgenic tobacco calli that are expressing the RLE3 esterase. It is believed that any member of the pyridine herbicide family that is deactivated by an esterase, and any esterase gene that can hydrolyze the methylester group of a pyridine herbicide would be able to function in this selection system.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied in the compositions or in the steps or sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

Armbruster et al., *Effects of the herbicide dithiopyr on cell division in wheat root tips*, Pest Biochem Physiol 39, 110–120 (1991).

Armbruster et al., *Herbicide MON 7200 alters regulation of tubulin polymerization in, wheat root tip cells*, Plant Physiol Suppl. 86, 97 (1988).

Birren et al., *Genome Analysis: Analyzing DNA,* 1, Cold Spring Harbor, N.Y. (1996)

Brown, et al., *Basis for soybean tolerance to thifensulfuron methyl, Pest.* Biochem. Physiol., 37, 303–313 (1990).

Bouhida et al., *An analysis of the complete sequence of a sugarcane bacilliform virus genome infectious to banana and rice.* Journal General Virology (1993) vol. 74 pp. 15–22.

Callis et al., Genes and Develop. 1:1183–1200 (1987)

Cheng et al. *Rice transformation by Agrobacterium infection.* Methods Biotechnol. (1998), 3 (Recombinant Proteins from Plants), pp. 1–9.

Coruzzi et al., *Tissue-specific and light-regulated expression of a pea nuclear gene encoding the small subunit of ribulose-1,5-bisphosphate.* EMBO J. (1984) vol. 3 pp. 1671–1679.

Feng et al., *In vitro transformation of dithiopyr by rat liver enzymes: conversion of methyl thioesters to acids by oxygenases,* Xenobiotica 21,1265–1271 (1991).

Feng, et al., *In vitro Transformation of Thiazopyr by Rat Liver Enzymes: Sulfur and Carbon Oxidations by Microsomes,* Pestic Biochem Physiol 48, 8–14 (1994a).

Feng et al., *In vitro Biotransformation of Thiazopyr by Rat Liver Microsomes: Oxidative Cleavage of Carboxylic Methylester by Monooxygenases,* Xenobiotica 24, 729–734 (1994b).

Feng et al., *Inhibition of Thiazopyr Metabolism in Plant Seedlings by Inhibitors of Monooxygenases,* Pesticide Sci 45, 203–207 (1995a).

Feng et al., *Metabolic deactivation of thiazopyr herbicide by animal liver esterases,* Xenobiotica 25, 27–35 (1995b).

Gallie et al., The Plant Cell 1:301–311 (1989).

Hinchee et al., Bio/Technology 6:915–922 (1988)

Hinchee et al., *Plant Transformation, In PLANT CELL AND TISSUE CULTURE,* 231–270, 1994, Vasil and Thorpe (Eds.), Dordrecht Publishing, Netherlands.

Horsch et al., *A simple and general method for transferring genes into plants,* Science 227, 1229–1231 (1985).

Kao et al., *Multiple forms of esterases in mouse, rat, rabbit liver, and their role in hydrolysis of organophosphorus and pyrethroid insecticides,* Pest. Biochem. Physiol., 23, 66–73 (1985).

Korza et al., *Complete covalent structure of a 60 kD esterase isolated from 2,3,7,8-tetrachlorodibenzo-p-dioxin induced rabbit liver microsomes,* J Biol Chem 263, 3486–3495 (1988).

Koziel et al., *Transgenic maize plants for the control of european corn borer.* Abstract, ACS annual meeting, Chicago, Ill., Aug. 22–27, 1993. (1993).

Koziel et al., *Plant Mol. Biol.* 32:393–405 (1996)

Krell et al., *Plant biochemistry of xenobiotics: purification and properties of a wheat esterase hydrolyzing the plasticizer chemical, bis(2-ethylhexyl)phthalate,* Eur. J. Biochem, 143, 57–62 (1984).

Leinweber, F. J., *Possible physiological roles of carboxylic ester hydrolases,* Drug Metab Reviews 18, 379–439 (1987).

Li et al., *Comparison of promoters and selectable marker genes for use in indica rice transformation.* Molecular Breeding (1997) vol. 3 pp. 1–14.

Long et al., *Rat liver carboxylesterase: cDNA cloning, sequencing, and evidence for a multigene family,* Biochem Biophys Res Comm 156, 866–873 (1988).

Maliga, Trends in Biotechnology 11, 101–106 (1993)

Mascarenkas et al., Plant Mol. Biol., 15, 913–920 (1990)

McBride et al., Bio/Technology, 13:362–365 (1995).

McClanahan et al., *In vitro metabolism of thiazopyr plant metabolites by rat liver enzymes,* Pest Biochem Physiol 51, 90–98 (1995).

McElroy et. al., *Plant Cell.* 2:163–71 (1990)

Medberry et al., *Identification of cis elements involved in commelina yellow mottle virus promoter activity.* Plant Journal (1993) vol. 3 pp. 619–626.

Mentlein et al., *Simultaneous purification and comparative characterization of six serine hydrolases from rat liver microsomes,* Archi. Biochem. Biophys., 200, 547–559 (1980).

Moffatt et al., *The adenine phosphoribosyltransferase-encoding gene of Arabidopsis thaliana.* Gene (1994) vol 143 pp. 211–216.

Ni et al. *Strength and tissue specificity of chimeric promoters derived from the octopine and mannopine synthase genes.* Plant J. (1995) vol. 7 pp. 661–676.

Nourse et al., *Purification and properties of an esterase from Cucurbita maxima fruit tissue,* Phytochem., 28, 379–383 (1989).

Odell et al., *Identification of DNA sequences required for activity of the cauliflower mosaic virus 35S promoter.* Nature (1985) vol. 313 pp. 810–812.

O'Reilly et al., *Baculovirus Expression Vectors: A Lab Manual,* W. H. Freeman & Co., Ozols, J., *Isolation, properties, and complete amino acid sequence of a second form of 60 kD glycoprotein esterase,* J Biol Chem 264,12533–12545 (1989).

Ozols, J., *Isolation and characterization of a 60-kilodalton glycoprotein esterase from liver microsomal membranes,* J Biol Chem 262, 15316–15321 (9187).

Potrykus et al., *Mol. Gen. Genet.* 199:183–188 (1985)

Rao et al., *Enhancement of Thiazopyr Bioefficacy by Inhibitors of Monooxygenases,* Pesticide Sci 45, 209–213 (1995).

Ritchie et al., *Cell Culture and Regeneration of Transgenic Plants,* 147–177, 1993, In TRANSGENIC PLANTS, Vol.

1, Kung and We (Eds.), Academic Press Inc, Harcourt Brace Jovanovich Publishers.

Robbi et al., *Nucleotide sequence of cDNA coding for rat liver pI 6.1 esterase (ES-10), a carboxylesterase located in the lumen of the endoplasmic reticulum*, Biochem J. 269, 451–458 (1990).

Saito et al. *Method of transforming monocotyledon by using scutellum of immature embryo.* WO 9506722 A1 (1995).

Sambrook et al., *Molecular Cloning: A Laboratory Manual*, Cold Spring Harbor Press (1989)

Sanger et al., *Characteristics of a strong promoter from figwort mosaic virus: comparison with the analogous 35S promoter from cauliflower mosaic virus and the regulated mannopine synthase promoter.* Plant Mol. Biol. (1990) vol. 14 pp. 433–443.

Schulz et al., *Genetic engineering of herbicide resistance in higher plants*, Critical Rev. Plant Sci., 9, 1–15 (1990).

Stalker et al., *J. Biol. Chem.* 263:6310–6314 (1988)

Thillet et al., *J. Biol. Chem.* 263:12500–12508 (1988)

Vasil et al., Plant Physiol. 91:1575–1579 (1989)

Xu et al., *Rice triosephosphate isomerase gene 5' sequence directs beta-glucuronidase activity in transgenic tobacco but requires an intron for expression in rice.* Plant Physiology (1994) vol. 106 pp. 459–467.

Zhong et al., *Analysis of the functional activity of the 1.4 kb 5' region of the rice actin 1 gene in stable transgenic plants of maize (Zea mays L.).* Plant Science (1996) vol. 116 pp. 73–84.

SEQUENCE LISTING

```
<160> NUMBER OF SEQ ID NOS: 11

<210> SEQ ID NO 1
<211> LENGTH: 539
<212> TYPE: PRT
<213> ORGANISM: Rabbit

<400> SEQUENCE: 1

His Pro Ser Ala Pro Pro Val Val Asp Thr Val Lys Gly Lys Val Leu
 1               5                  10                  15

Gly Lys Phe Val Ser Leu Glu Gly Phe Ala Gln Pro Val Ala Val Phe
            20                  25                  30

Leu Gly Val Pro Phe Ala Lys Pro Pro Leu Gly Ser Leu Arg Phe Ala
        35                  40                  45

Pro Pro Gln Pro Ala Glu Ser Trp Ser His Val Lys Asn Thr Thr Ser
    50                  55                  60

Tyr Pro Pro Met Cys Ser Ser Asp Ala Val Ser Gly His Met Leu Ser
65                  70                  75                  80

Glu Leu Phe Thr Asn Arg Lys Glu Asn Ile Pro Leu Lys Phe Ser Glu
                85                  90                  95

Asp Cys Leu Tyr Leu Asn Ile Tyr Thr Pro Ala Asp Leu Thr Lys Arg
            100                 105                 110

Gly Arg Leu Pro Val Met Val Trp Ile His Gly Gly Gly Leu Met Val
        115                 120                 125

Gly Gly Ala Ser Thr Tyr Asp Gly Leu Ala Leu Ser Ala His Glu Asn
    130                 135                 140

Val Val Val Val Thr Ile Gln Tyr Arg Leu Gly Ile Gly Gly Phe Gly
145                 150                 155                 160

Phe Asn Ile Asp Glu Leu Phe Leu Val Ala Val Asn Arg Trp Val Gln
                165                 170                 175

Asp Asn Ile Ala Asn Phe Gly Gly Asp Pro Gly Ser Val Thr Ile Phe
            180                 185                 190

Gly Glu Ser Ala Gly Gly Gln Ser Val Ser Ile Leu Leu Leu Ser Pro
        195                 200                 205

Leu Thr Lys Asn Leu Phe His Arg Ala Ile Ser Glu Ser Gly Val Ala
    210                 215                 220

Leu Leu Ser Ser Leu Phe Arg Lys Asn Thr Lys Ser Leu Ala Glu Lys
225                 230                 235                 240

Ile Ala Ile Glu Ala Gly Cys Lys Thr Thr Thr Ser Ala Val Met Val
                245                 250                 255
```

His Cys Leu Arg Gln Lys Thr Glu Glu Leu Met Glu Val Thr Leu
                260                 265                 270

Lys Met Lys Phe Met Ala Leu Asp Leu Val Gly Asp Pro Lys Glu Asn
            275                 280                 285

Thr Ala Phe Leu Thr Thr Val Ile Asp Gly Val Leu Leu Pro Lys Ala
        290                 295                 300

Pro Ala Glu Ile Tyr Glu Lys Lys Tyr Asn Met Leu Pro Tyr Met
305                 310                 315                 320

Val Gly Ile Asn Gln Gln Glu Phe Gly Trp Ile Ile Pro Met Gln Met
                325                 330                 335

Leu Gly Tyr Pro Leu Ser Glu Gly Lys Leu Asp Gln Lys Thr Ala Thr
            340                 345                 350

Glu Leu Leu Trp Lys Ser Tyr Pro Ile Val Asn Val Ser Lys Glu Leu
        355                 360                 365

Thr Pro Val Ala Thr Glu Lys Tyr Leu Gly Gly Thr Asp Asp Pro Val
    370                 375                 380

Lys Lys Lys Asp Leu Phe Leu Asp Met Leu Ala Asp Leu Leu Phe Gly
385                 390                 395                 400

Val Pro Ser Val Asn Val Ala Arg His His Arg Asp Ala Gly Ala Pro
                405                 410                 415

Thr Tyr Met Tyr Glu Tyr Arg Tyr Arg Pro Ser Phe Ser Ser Asp Met
            420                 425                 430

Arg Pro Lys Thr Val Ile Gly Asp His Gly Asp Glu Ile Phe Ser Val
        435                 440                 445

Leu Gly Ala Pro Phe Leu Lys Glu Gly Ala Thr Glu Glu Glu Ile Lys
    450                 455                 460

Leu Ser Lys Met Val Met Lys Tyr Trp Ala Asn Phe Ala Arg Asn Gly
465                 470                 475                 480

Asn Pro Asn Gly Glu Gly Leu Pro Gln Trp Pro Ala Tyr Asp Tyr Lys
                485                 490                 495

Glu Gly Tyr Leu Gln Ile Gly Ala Thr Thr Gln Ala Ala Gln Lys Leu
            500                 505                 510

Lys Asp Lys Glu Val Ala Phe Trp Thr Glu Leu Trp Ala Lys Glu Ala
        515                 520                 525

Ala Arg Pro Arg Glu Thr Glu His Ile Glu Leu
    530                 535

<210> SEQ ID NO 2
<211> LENGTH: 566
<212> TYPE: PRT
<213> ORGANISM: Rabbit

<400> SEQUENCE: 2

Met Ala Arg Leu Tyr Pro Leu Val Trp Leu Phe Leu Ala Ala Cys Thr
1               5                   10                  15

Ala Trp Gly His Pro Ser Ala Pro Pro Val Val Asp Thr Val Lys Gly
                20                  25                  30

Lys Val Leu Gly Lys Phe Val Ser Leu Glu Gly Phe Ala Gln Pro Val
            35                  40                  45

Ala Val Phe Leu Gly Val Pro Phe Ala Lys Pro Pro Leu Gly Ser Leu
        50                  55                  60

Arg Phe Ala Pro Pro Gln Pro Ala Glu Ser Trp Ser His Val Lys Asn
65                  70                  75                  80

Thr Thr Ser Tyr Pro Pro Met Cys Ser Gln Asp Ala Val Ser Gly His

```
                        85                      90                      95
Met Leu Ser Glu Leu Phe Thr Asn Arg Lys Glu Asn Ile Pro Leu Lys
            100                     105                     110

Phe Ser Glu Asp Cys Leu Tyr Leu Asn Ile Tyr Thr Pro Ala Asp Leu
            115                     120                     125

Thr Lys Arg Gly Arg Leu Pro Val Met Val Trp Ile His Gly Gly Gly
            130                     135                     140

Leu Met Val Gly Gly Ala Ser Thr Tyr Asp Gly Leu Ala Leu Ser Ala
145                     150                     155                 160

His Glu Asn Val Val Val Thr Ile Gln Tyr Arg Leu Gly Ile Trp
                165                     170                     175

Gly Phe Phe Ser Thr Gly Asp Glu His Ser Arg Gly Asn Trp Gly His
            180                     185                     190

Leu Asp Gln Val Arg Ala Leu Arg Trp Val Gln Asp Asn Ile Ala Asn
            195                     200                     205

Phe Gly Gly Asp Pro Gly Ser Val Thr Ile Phe Gly Glu Ser Ala Gly
            210                     215                     220

Gly Gln Ser Val Ser Ile Leu Leu Ser Pro Leu Thr Lys Asn Leu
225                     230                     235                 240

Phe His Arg Ala Ile Ser Glu Ser Gly Val Ala Leu Leu Ser Ser Leu
            245                     250                     255

Phe Arg Lys Asn Thr Lys Ser Leu Ala Glu Lys Ile Ala Ile Glu Ala
            260                     265                     270

Gly Cys Lys Thr Thr Thr Ser Ala Val Met Val His Cys Leu Arg Gln
            275                     280                     285

Lys Thr Glu Glu Glu Leu Met Glu Val Thr Leu Lys Met Lys Phe Met
290                     295                     300

Ala Leu Asp Leu Val Gly Asp Pro Lys Glu Asn Thr Ala Phe Leu Thr
305                     310                     315                 320

Thr Val Ile Asp Gly Val Leu Leu Pro Lys Ala Pro Ala Glu Ile Leu
            325                     330                     335

Ala Glu Lys Lys Tyr Asn Met Leu Pro Tyr Met Val Gly Ile Asn Gln
            340                     345                     350

Gln Glu Phe Gly Trp Ile Ile Pro Met Gln Met Leu Gly Tyr Pro Leu
            355                     360                     365

Ser Glu Gly Lys Leu Asp Gln Lys Thr Ala Thr Glu Leu Leu Trp Lys
370                     375                     380

Ser Tyr Pro Ile Val Asn Val Ser Lys Glu Leu Thr Pro Val Ala Thr
385                     390                     395                 400

Glu Lys Tyr Leu Gly Gly Thr Asp Asp Pro Val Lys Lys Lys Asp Leu
            405                     410                     415

Phe Leu Asp Met Leu Ala Asp Leu Leu Phe Gly Val Pro Ser Val Asn
            420                     425                     430

Val Ala Arg His His Arg Asp Ala Gly Ala Pro Thr Tyr Met Tyr Glu
            435                     440                     445

Tyr Arg Tyr Arg Pro Ser Phe Ser Ser Asp Met Arg Pro Lys Thr Val
            450                     455                     460

Ile Gly Asp His Gly Asp Glu Ile Phe Ser Val Leu Gly Ala Pro Phe
465                     470                     475                 480

Leu Lys Glu Gly Ala Thr Glu Glu Glu Ile Lys Leu Ser Lys Met Val
            485                     490                     495

Met Lys Tyr Trp Ala Asn Phe Ala Arg Asn Gly Asn Pro Asn Gly Glu
            500                     505                     510
```

```
Gly Leu Pro Gln Trp Pro Ala Tyr Asp Tyr Lys Glu Gly Tyr Leu Gln
            515                 520                 525

Ile Gly Ala Thr Thr Gln Ala Ala Gln Lys Leu Lys Asp Lys Glu Val
        530                 535                 540

Ala Phe Trp Thr Glu Leu Trp Ala Lys Glu Ala Ala Arg Pro Arg Glu
545                 550                 555                 560

Thr Glu His Ile Glu Leu
                565

<210> SEQ ID NO 3
<211> LENGTH: 1701
<212> TYPE: DNA
<213> ORGANISM: Rabbit

<400> SEQUENCE: 3
```

| | | | | |
|---|---|---|---|---|
| atggcaagac | tctacccact | cgtgtggctc | ttccttgcag | cctgcaccgc atggggtcac | 60 |
| ccctccgcac | cacctgtggt | tgacactgta | aggggaaag | tcctgggaa gttcgtcagc | 120 |
| ttagaaggat | ttgcacagcc | cgtggccgtc | ttcctgggag | tccccttcgc caagcccct | 180 |
| cttggatccc | tgaggtttgc | accaccacag | cctgcagaat | catggagcca cgtgaagaac | 240 |
| accacctcct | accctcccat | gtgctcccag | gacgcagtat | cagggcatat gctctcggag | 300 |
| ctcttcacca | acagaaaaga | gaacatccct | cttaagtttt | ctgaagactg cctttacctg | 360 |
| aatatttaca | cccctgctga | cctgacaaag | agaggcaggc | tgccggtgat ggtgtggatc | 420 |
| catggaggtg | gtctgatggt | gggtggagca | tcaacctatg | atggcctggc tctttctgcc | 480 |
| catgagaacg | tggtggtggt | gaccattcag | taccgcctgg | gcatctgggg attcttcagc | 540 |
| acaggagatg | agcacagccg | agggaactgg | ggtcacttgg | accaggtgcg tgcgctgcgg | 600 |
| tgggtccagg | acaatattgc | caactttgga | ggggacccag | gctctgtgac catctttgga | 660 |
| gagtcagcag | gaggtcaaag | tgtctctatc | cttctattat | ccccctgac caagaatctc | 720 |
| ttccatcgag | caatttccga | gagtggcgt | gccctccttt | ccagtctctt caggaagaac | 780 |
| accaagtcct | tggctgagaa | aattgccatc | gaagctgggt | gtaaaaccac cacctcggct | 840 |
| gtcatggttc | actgcctgcg | ccagaagaca | gaggaagaac | tcatggaggt gacattgaaa | 900 |
| atgaaattta | tggctctaga | tctagttggc | gaccccaaag | agaacaccgc cttcctgacc | 960 |
| actgtgattg | atgggggtgct | gctgccaaaa | gcacctgcag | agattctggc agagaagaaa | 1020 |
| tacaacatgc | tgccctacat | ggtgggaatc | aaccagcaag | agtttggctg gattatccca | 1080 |
| atgcaaatgc | tgggctatcc | actctctgaa | ggcaaactgg | accagaagac agctacagaa | 1140 |
| ctcttgtgga | agtcctaccc | cattgtcaat | gtctctaagg | agctgactcc agtggccact | 1200 |
| gagaagtatt | taggagggac | agatgaccct | gtcaaaaaga | aagacttgtt cctggacatg | 1260 |
| cttgcagatt | tgttatttgg | tgtcccatct | gtgaatgtgc | tcgtcacca cagagatgct | 1320 |
| ggagccccca | cctatatgta | tgagtatcgg | tatcgcccaa | gcttctcatc agacatgaga | 1380 |
| cccaagacag | tgataggggga | ccatggagat | gagatcttct | ctgtcttagg agccccgttt | 1440 |
| ttaaaagagg | gtgccacaga | agaggagatc | aaactgagca | agatggtgat gaaatactgg | 1500 |
| gccaactttg | ctaggaatgg | gaatcccaat | ggagaagggc | ttcctcaatg ccagcatat | 1560 |
| gactacaagg | aaggttacct | gcagattgga | gccaccaccc | aggcagccca gaaactgaaa | 1620 |
| gacaaggaag | tggctttctg | gactgagctc | tgggccaagg | aggcagcaag gccacgtgag | 1680 |
| actgaacaca | tcgagctgta | g | | | 1701 |

<210> SEQ ID NO 4
<211> LENGTH: 55
<212> TYPE: DNA
<213> ORGANISM: Artificial Sequence
<220> FEATURE:
<223> OTHER INFORMATION: amino terminal degenerate synthetic amplification
      primer based on published amino acid sequence of
      rabbit liver esterase isozyme 1 RLE1(Ozols, 1987);
      n44 & n50 = a, c, g, or t

<400> SEQUENCE: 4
gcaccatggc ccacccctcc gcaccacctg tggttgacac tgtnaarggn aargt          55

<210> SEQ ID NO 5
<211> LENGTH: 36
<212> TYPE: DNA
<213> ORGANISM: Artificial Sequence
<220> FEATURE:
<223> OTHER INFORMATION: carboxy terminal degenerate synthetic
      amplification primer based on published amino acid
      sequence of rabbit liver esterase isozyme 1
      RLE1(Ozols, 1987); n31 = a, c, g, or t

<400> SEQUENCE: 5
cgctctagag ctctacagyt cgatrtgytc ngtytc                              36

<210> SEQ ID NO 6
<211> LENGTH: 56
<212> TYPE: DNA
<213> ORGANISM: Artificial Sequence
<220> FEATURE:
<223> OTHER INFORMATION: Description of Artificial Sequence: synthetic
      sequence coding for ER signal peptide based on
      Robbi et al., 1990

<400> SEQUENCE: 6
catggcaaga ctctacccac tcgtgtggct cttccttgca gcctgcaccg catggg        56

<210> SEQ ID NO 7
<211> LENGTH: 57
<212> TYPE: DNA
<213> ORGANISM: Artificial Sequence
<220> FEATURE:
<223> OTHER INFORMATION: Description of Artificial Sequence: synthetic
      inverse strand sequence coding for ER signal
      peptide based on Robbi et al., 1990

<400> SEQUENCE: 7
gtgaccccat gcggtgcagg ctgcaaggaa gagccacacg agtgggtaga gtcttgc       57

<210> SEQ ID NO 8
<211> LENGTH: 47
<212> TYPE: DNA
<213> ORGANISM: Artificial Sequence
<220> FEATURE:
<223> OTHER INFORMATION: Description of Artificial Sequence: synthetic
      thermal amplification sequence homologous to RLE3
      divergent region flanking sequence

<400> SEQUENCE: 8
aactcatcga tgttgaaacc gaagccaccg atgcccaggc ggtactg                  47

<210> SEQ ID NO 9
<211> LENGTH: 53
<212> TYPE: DNA
<213> ORGANISM: Artificial Sequence
<220> FEATURE:
<223> OTHER INFORMATION: Description of Artificial Sequence: synthetic -continued

```
      thermal amplification sequence homologous to RLE1
      divergent divergent region flanking sequence

<400> SEQUENCE: 9
tcaacatcga tgagttgttc ttggtggctg tgaaccggtg ggtccaggac aat        53

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: synthetic site
      specific mutagenesis primer for RLE3 amino acid
      sequence conversion of Gln71Ser

<400> SEQUENCE: 10
cccatgtgct cctccgacgc agtatcagg                                   29

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: synthetic site
      specific mutagenesis primer for RLE3 amino acid
      sequence conversion of Leu309Tyr and Ala310Glu.

<400> SEQUENCE: 11
gcacctgcag agatttacga ggagaagaaa tacaacatgc                       40
```

What is claimed is:

1. A recombinant polynucleotide molecule comprising a plant functional promoter operably linked to a polynucleotide sequence encoding an esterase that catalyzes the hydrolysis of an alkyl ester group of a pyridine herbicide compound, wherein said esterase comprises the amino acid sequence His-Ser-Arg-Gly-Asn-Try-Gly-His.

2. The polynucleotide molecule of claim 1, wherein the esterase coding sequence is isolated from rabbit, porcine, bovine, pigeon, goat, horse, or sheep.

3. The polynucleotide molecule of claim 2, wherein the esterase coding sequence comprises rabbit RLE3.

4. The polynucleotide molecule of claim 1, wherein the pyridine compound is thiazopyr or MON14300.

5. A method for selecting transformed plant cells, comprising the steps of:
   (a) transforming plant cells with a recombinant polynucleotide molecule which comprises:
      (i) a sequence comprising a promoter that functions in plant cells to cause the production of an RNA molecule; operably linked to,
      (ii) a polynucleotide sequence encoding an esterase that catalyzes the hydrolysis of an alkyl ester group of an herbicidally active pyridine; and
      (iii) a 3' non-translated region that functions in plant cells to cause the polyadenylation of the 3' end of the RNA molecule; and
   (b) selecting those transformed cells which survive exposure to the pyridine, wherein said esterase comprises the amino acid sequence His-Ser-Arg-Gly-Asn-Trp-Gly-His.

6. The method of claim 5, wherein the esterase coding sequence is isolated from rabbit, porcine, bovine, pigeon, goat, horse, or sheep.

7. The method of claim 6, wherein the esterase coding sequence comprises rabbit RLE3.

8. The method of claim 5, wherein the pyridine is thiazopyr or MON 14300.

9. A method for the production of pyridine resistant transgenic plants, comprising the steps of:
   (a) transforming plant cells with a polynucleotide molecule comprising:
      (i) a promoter that functions in plant cells to cause the production of an RNA molecule; operably linked to,
      (ii) a polynucleotide sequence encoding an esterase that catalyzes the hydrolysis of an alkyl ester group of an herbicidally active pyridine; and
      (iii) a 3' non-translated region that functions in plant cells to cause the polyadenylation of the 3' end of the RNA molecule;
   (b) selecting transformed cells; and
   (c) regenerating a plant from the selected transformed plant cells, wherein said esterase comprises the amino acid sequence His-Ser-Arg-Gly-Asn-Trp-Gly-His.

10. The method of claim 9, wherein the esterase coding sequence is isolated from rabbit, porcine, bovine, pigeon, goat, horse, or sheep.

11. The method of claim 9, wherein the esterase coding sequence comprises rabbit RLE3.

12. The method of claim 9, wherein the pyridine is thiazopyr or MON 14300.

13. A recombinant polynucleotide molecule comprising:
   (a) a promoter that functions in plant cells to cause the production of an RNA molecule; operably linked to,
   (b) a polynucleotide sequence encoding an esterase that catalyzes the hydrolysis of an alkyl ester group of an herbicidally active pyridine; and
   (c) a 3' non-translated region that functions in plant cells to cause the polyadenylation of the 3' end of the RNA molecule;

wherein said esterase comprises the amino acid sequence His-Ser-Arg-Gly-Asn-Trp-Gly-His.

14. The polynucleotide molecule of claim 3 wherein said RLE3 comprises the sequence as set forth in SEQ ID NO:2.

15. The method of claim 7, wherein said RLE3 comprises the sequence as set forth in SEQ ID NO:2.

16. The method of claim 9, wherein the esterase coding sequence comprises rabbit RLE3.

17. A polynucleotide sequence encoding an esterase that catalyzes the hydrolysis of an alkyl ester group of an herbicidally active pyridine, said esterase comprising the amino acid sequence His-Ser-Arg-Gly-Asn-Trp-Gly-His.

18. The polynucleotide sequence of claim 17, wherein the esterase coding sequence is isolated from rabbit, porcine, bovine, pigeon, goat, horse, or sheep.

19. The polynucleotide sequence of claim 18, wherein the esterase coding sequence comprises the rabbit RLE3 gene coding sequence as set forth in SEQ ID NO:3.

20. The polynucleotide sequence of claim 19, wherein said esterase comprises the sequence as set forth in SEQ ID NO:2.

21. The polynucleotide sequence of claim 20, wherein the pyridine is thiazopyr or MON 14300.

22. A plant cell expressing a polypeptide comprising an esterase that catalyzes the hydrolysis of an alkyl ester group of an herbicidally active pyridine, wherein said esterase comprises the amino acid sequence His-Ser-Arg-Gly-Asn-Trp-Gly-His, and wherein said esterase is encoded by a nucleotide sequence isolated and purified from other than a plant source.

23. The plant cell of claim 22, wherein said esterase comprises the sequence as set forth in SEQ ID NO:2.

24. The plant cell of claim 23, wherein said esterase coding sequence comprises the sequence as set forth in SEQ ID NO:3.

25. The plant cell of claim 24, wherein the pyridine is thiazopyr or MON 14300.

26. A plant cell comprising an esterase activity that catalyzes the hydrolysis of an alkyl ester group of an herbicidally active pyridine, wherein said esterase comprises the amino acid sequence His-Ser-Arg-Gly-Asn-Trp-Gly-His.

27. The plant cell of claim 26, wherein said esterase comprises the sequence as set forth in SEQ ID NO:2.

28. The plant cell of claim 27, wherein the pyridine is thiazopyr or MON 14300.

29. The plant cell of claim 28 wherein the esterase is produced by expression of a polynucleotide sequence isolated from rabbit, porcine, bovine, pigeon, goat, horse, or sheep.

30. A plant comprising an esterase that catalyzes the hydrolysis of an alkyl ester group of an herbicidally active pyridine, wherein said esterase comprises the amino acid sequence His-Ser-Arg-Gly-Asn-Trp-Gly-His, and wherein said esterase is encoded by a nucleotide sequence isolated and purified from other than a plant source.

31. A seed from the plant of claim 30, wherein said seed comprises said amino acid sequence.

32. A method for identifying an esterase that catalyzes the hydrolysis of an alkyl ester group of an herbicidally active pyridine, comprising the steps of:

a) identifying pyridine esterase activity in a biological sample or biological sample extract;

b) purifying esterase activity from said sample or sample extract;

c) identifying purified esterase activity as a protein;

d) isolating and purifying said protein; and e) identifying the amino acid sequence His-Ser-Arg-Gly-Asn-Trp-Gly-His in said purified protein by contacting said purified protein with antibodies specific for the amino acid sequence;

wherein said esterase comprises the amino acid sequence His-Ser-Arg-Gly-Asn-Trp-Gly-His.

* * * * *